(12) United States Patent
Minoguchi et al.

(10) Patent No.: US 10,828,208 B2
(45) Date of Patent: Nov. 10, 2020

(54) LOW-BULK, CLOSE-FITTING, HIGH-CAPACITY DISPOSABLE ABSORBENT PANT

(71) Applicant: The Procter & Gamble Company, Cincinnati, OH (US)

(72) Inventors: Ryo Minoguchi, Cincinnati, OH (US); Fred Naval Desai, Fairfield, OH (US); Alexander Fedotov, Schwalbach am Taunus (DE)

(73) Assignee: The Procte & Gamble Company, Cincinnati, OH (US)

( * ) Notice: Subject to any disclaimer, the term of this patent is extended or adjusted under 35 U.S.C. 154(b) by 773 days.

(21) Appl. No.: 15/357,280

(22) Filed: Nov. 21, 2016

(65) Prior Publication Data
US 2018/0140477 A1 May 24, 2018

(51) Int. Cl.
*A61F 13/15* (2006.01)
*A61F 13/496* (2006.01)
(Continued)

(52) U.S. Cl.
CPC ........ *A61F 13/4963* (2013.01); *A61F 13/496* (2013.01); *A61F 13/49007* (2013.01);
(Continued)

(58) Field of Classification Search
CPC .......... A61F 13/49007; A61F 13/49061; A61F 13/496; A61F 13/513; A61F 13/51464;
(Continued)

(56) References Cited

U.S. PATENT DOCUMENTS

| 4,340,706 A | 7/1982 | Obayashi et al. |
| 4,507,438 A | 3/1985 | Obayashi et al. |

(Continued)

FOREIGN PATENT DOCUMENTS

| DE | 10204937 A1 | 8/2003 |
| JP | 2013-111419 | 6/2013 |

(Continued)

OTHER PUBLICATIONS

PCT International Search Report dated Feb. 5, 2018 (13 pages).

*Primary Examiner* — Jacqueline F Stephens
(74) *Attorney, Agent, or Firm* — William E. Gallagher

(57) ABSTRACT

A low bulk, high capacity disposable absorbent pant is disclosed. The pant may have a variety of combinations of features that contribute to imparting the pant with a more close-fitting, discreet appearance, particularly under outer clothing, more resembling that of an ordinary undergarment. The features may include an arrangement of relatively closely-spaced elastomeric strands in a belt structure; elastomeric strands in the belt structure having active portions that traverse forward and rearward portions of an absorbent pad assembly; an arrangement of elastomeric strands in the belt structure below the side seams; an arrangement of longitudinal elastic strands in the absorbent pad assembly that are closer to the longitudinal axis of the pant than to the side seams; and/or an absorbent core structure having portions that are tapered and/or channeled.

17 Claims, 8 Drawing Sheets

(51) Int. Cl.
*A61F 13/534* (2006.01)
*A61F 13/514* (2006.01)
*A61F 13/537* (2006.01)
*A61F 13/49* (2006.01)
*A61F 13/513* (2006.01)

(52) U.S. Cl.
CPC ...... *A61F 13/49061* (2013.01); *A61F 13/513* (2013.01); *A61F 13/51464* (2013.01); *A61F 13/534* (2013.01); *A61F 13/537* (2013.01); *A61F 2013/49044* (2013.01); *A61F 2013/49092* (2013.01); *A61F 2013/49093* (2013.01); *A61F 2013/51322* (2013.01)

(58) Field of Classification Search
CPC .......... A61F 13/537; A61F 2013/49044; A61F 2013/49092; A61F 2013/49093; A61F 2013/51322
USPC ............ 604/385.24, 385.25, 385.26, 385.27, 604/385.29, 385.3
See application file for complete search history.

(56) References Cited

U.S. PATENT DOCUMENTS

| | | | |
|---|---|---|---|
| 4,666,983 A | 5/1987 | Tsubankimoto et al. | |
| 5,266,392 A | 11/1993 | Land | |
| 5,281,683 A | 1/1994 | Yano et al. | |
| 5,331,059 A | 7/1994 | Engelhardt et al. | |
| 5,340,648 A | 8/1994 | Rollins | |
| 5,409,711 A | 4/1995 | Dahmen et al. | |
| 5,501,756 A | 3/1996 | Rollins | |
| 5,507,909 A | 4/1996 | Rollins | |
| 5,532,323 A | 7/1996 | Yano et al. | |
| 5,574,121 A | 11/1996 | Irie et al. | |
| 5,837,789 A | 11/1998 | Stockhausen et al. | |
| 5,849,816 A | 12/1998 | Suskind et al. | |
| 6,077,375 A | 6/2000 | Kwok | |
| 6,143,821 A | 11/2000 | Houben | |
| 6,200,635 B1 | 3/2001 | Kwok | |
| 6,235,137 B1 | 5/2001 | Van Esperen | |
| 6,265,488 B1 | 7/2001 | Fujino et al. | |
| 6,361,634 B1 | 3/2002 | White | |
| 6,472,478 B1 | 10/2002 | Funk et al. | |
| 6,503,979 B1 | 1/2003 | Funk et al. | |
| 6,520,237 B1 | 2/2003 | Bolyard | |
| 6,559,239 B1 | 5/2003 | Riegel et al. | |
| 6,582,518 B2 | 6/2003 | Riney | |
| 6,610,161 B2 | 8/2003 | Erdman | |
| 6,613,146 B2 | 9/2003 | Bolyard | |
| 6,632,385 B2 | 10/2003 | Kauschke | |
| 6,645,569 B2 | 11/2003 | Cramer | |
| 6,652,693 B2 | 11/2003 | Buriss | |
| 6,657,015 B1 | 12/2003 | Riegel et al. | |
| 6,719,846 B2 | 4/2004 | Nakamura | |
| 6,737,102 B1 | 5/2004 | Saidman | |
| 6,803,103 B2 | 10/2004 | Kauschke | |
| 6,809,158 B2 | 10/2004 | Ikeuchi et al. | |
| 6,863,933 B2 | 3/2005 | Cramer | |
| 7,112,621 B2 | 9/2006 | rohrbaugh | |
| 7,199,211 B2 | 4/2007 | Popp et al. | |
| 7,250,481 B2 | 7/2007 | Jaworek et al. | |
| 7,652,111 B2 | 1/2010 | Hermeling et al. | |
| 7,687,596 B2 | 3/2010 | Hermeling et al. | |
| 7,744,576 B2 | 6/2010 | Busam et al. | |
| 7,772,420 B2 | 8/2010 | Hermeling et al. | |
| 7,838,722 B2 | 11/2010 | Blessing et al. | |
| 7,901,391 B2 | 3/2011 | Otsubo | |
| 8,124,229 B2 | 2/2012 | Stueven et al. | |
| 8,180,603 B2 | 5/2012 | Blessing et al. | |
| 8,186,296 B2 | 5/2012 | Brown | |
| 8,236,715 B2 | 8/2012 | Schmidt et al. | |
| 8,389,658 B2 | 3/2013 | Stueven et al. | |
| 8,581,019 B2 | 11/2013 | Carlucci et al. | |
| 8,728,051 B2 | 5/2014 | Lu | |
| 8,748,000 B2 | 6/2014 | Stueven et al. | |
| 8,939,957 B2 | 1/2015 | Raycheck | |
| 8,979,815 B2 | 3/2015 | Roe et al. | |
| 9,023,006 B2 | 5/2015 | Takino et al. | |
| 9,060,904 B2 | 6/2015 | Hundorf et al. | |
| 9,072,634 B2 | 7/2015 | Hundorf et al. | |
| 9,375,358 B2 | 6/2016 | Ehrnsperger et al. | |
| 2002/0197695 A1 | 12/2002 | Gluckmann et al. | |
| 2003/0148684 A1 | 8/2003 | Cramer | |
| 2005/0008839 A1 | 1/2005 | Cramer | |
| 2005/0010188 A1* | 1/2005 | Glaug ............... | A61F 13/15577 604/396 |
| 2005/0165208 A1 | 7/2005 | Popp et al. | |
| 2006/0057921 A1 | 3/2006 | Turi et al. | |
| 2007/0073262 A1* | 3/2007 | Babusik ............ | A61F 13/15699 604/396 |
| 2007/0093767 A1 | 4/2007 | Carlucci et al. | |
| 2008/0312619 A1 | 12/2008 | Ashton et al. | |
| 2008/0312620 A1 | 12/2008 | Ashton et al. | |
| 2008/0312621 A1 | 12/2008 | Hundorf et al. | |
| 2008/0312622 A1 | 12/2008 | Hundorf et al. | |
| 2008/0312628 A1 | 12/2008 | Hundorf et al. | |
| 2009/0318884 A1 | 12/2009 | Meyer et al. | |
| 2010/0040826 A1 | 2/2010 | Autran | |
| 2011/0071488 A1* | 3/2011 | Kuwano ........... | A61F 13/49001 604/385.3 |
| 2012/0316526 A1 | 12/2012 | Rosati et al. | |
| 2012/0316528 A1 | 12/2012 | Kreuzer et al. | |
| 2013/0213355 A1 | 8/2013 | Nishikawa et al. | |
| 2013/0226120 A1* | 8/2013 | Van De Maele ... | A61F 13/5323 604/372 |
| 2014/0031782 A1 | 1/2014 | Ichikawa et al. | |
| 2014/0163503 A1 | 6/2014 | Arizti et al. | |
| 2014/0163511 A1 | 6/2014 | Roe et al. | |
| 2014/0371701 A1 | 12/2014 | Bianchi et al. | |
| 2016/0128875 A1 | 5/2016 | Ichikawa | |
| 2016/0270971 A1 | 9/2016 | Raycheck et al. | |
| 2016/0270973 A1 | 9/2016 | Raycheck et al. | |
| 2016/0270975 A1 | 9/2016 | Prakash et al. | |
| 2016/0270978 A1 | 9/2016 | Prakash et al. | |
| 2016/0270979 A1 | 9/2016 | Prakash et al. | |
| 2016/0270980 A1 | 9/2016 | Raycheck et al. | |
| 2016/0270981 A1 | 9/2016 | Raycheck et al. | |
| 2016/0270983 A1 | 9/2016 | Roe et al. | |
| 2016/0270985 A1 | 9/2016 | Raycheck et al. | |

FOREIGN PATENT DOCUMENTS

| | | |
|---|---|---|
| JP | 2013-255573 | 12/2013 |
| WO | WO 1990-15830 A1 | 12/1990 |
| WO | WO 1993-21237 A1 | 10/1993 |
| WO | WO 2009-155265 A2 | 12/2009 |

\* cited by examiner

LOW-BULK, CLOSE-FITTING, HIGH-CAPACITY DISPOSABLE ABSORBENT PANT

BACKGROUND OF THE INVENTION

In recent years populations in many developed countries have shifted toward middle-aged and older demographic groups. These demographic groups represent markets with relatively increased demands for products and services addressed to concerns associated with aging.

One such concern is adult urinary incontinence. Urinary incontinence can result from or be exacerbated by a variety of health conditions, or even normal experiences such as childbearing.

Disposable absorbent pants for persons suffering from urinary incontinence have been marketed for a number of years. These products have traditionally been very similar to disposable baby diapers or disposable children's training pants, the main difference being size. One design type is known as the "belted" or "balloon" type pant, which is formed of a broad belt that encircles the wearer's waist and lower torso, bridged by a structure that connects front and rear belt portions through the wearer's crotch area. The crotch structure includes an absorbent structure designed to receive, contain and store urine until the time the pant is changed. The belt is typically formed of a stretch laminate material.

Due to their design and method of manufacture, the products may visually resemble a disposable baby diaper or training pant, rather than an ordinary undergarment. The crotch structure may tend to be bulky as a result of the presence of absorbent materials. The structure may have the appearance of a mass-produced disposable article, like a disposable child diaper. The belt structure, typically formed of a stretch laminate material, may also have a bulky, mass-produced, diaper-like appearance.

This resemblance has been a source of anxiety and discomfort for users. The bulk may cause outer clothing to fit poorly, or make it visibly apparent that an absorbent undergarment is being worn. Many users may be unhappy using products that may be associated with aging and loss of control of bodily functions, and may be embarrassed when their use of such products is visibly apparent to others.

In these circumstances, any improvement to traditional designs and materials for adult incontinence pants, which is efficient for manufacturing while providing an appearance, fitted profile and/or feel more closely resembling those of an ordinary undergarment, may provide competitive advantages to the manufacturer thereof.

DETAILED DESCRIPTION OF EXAMPLES

Definitions

Figure 1:
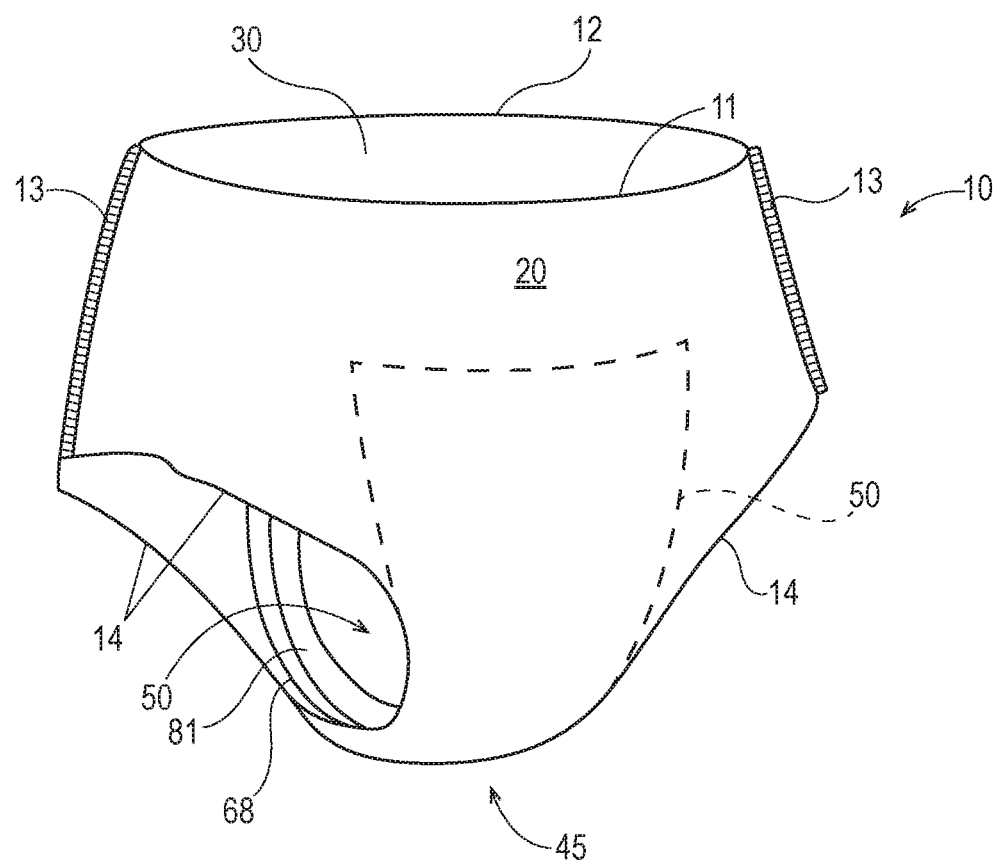
FIG. 1 is a schematic perspective view of an example of a pant as it might appear while being worn (wearer not shown).
Figure 2:
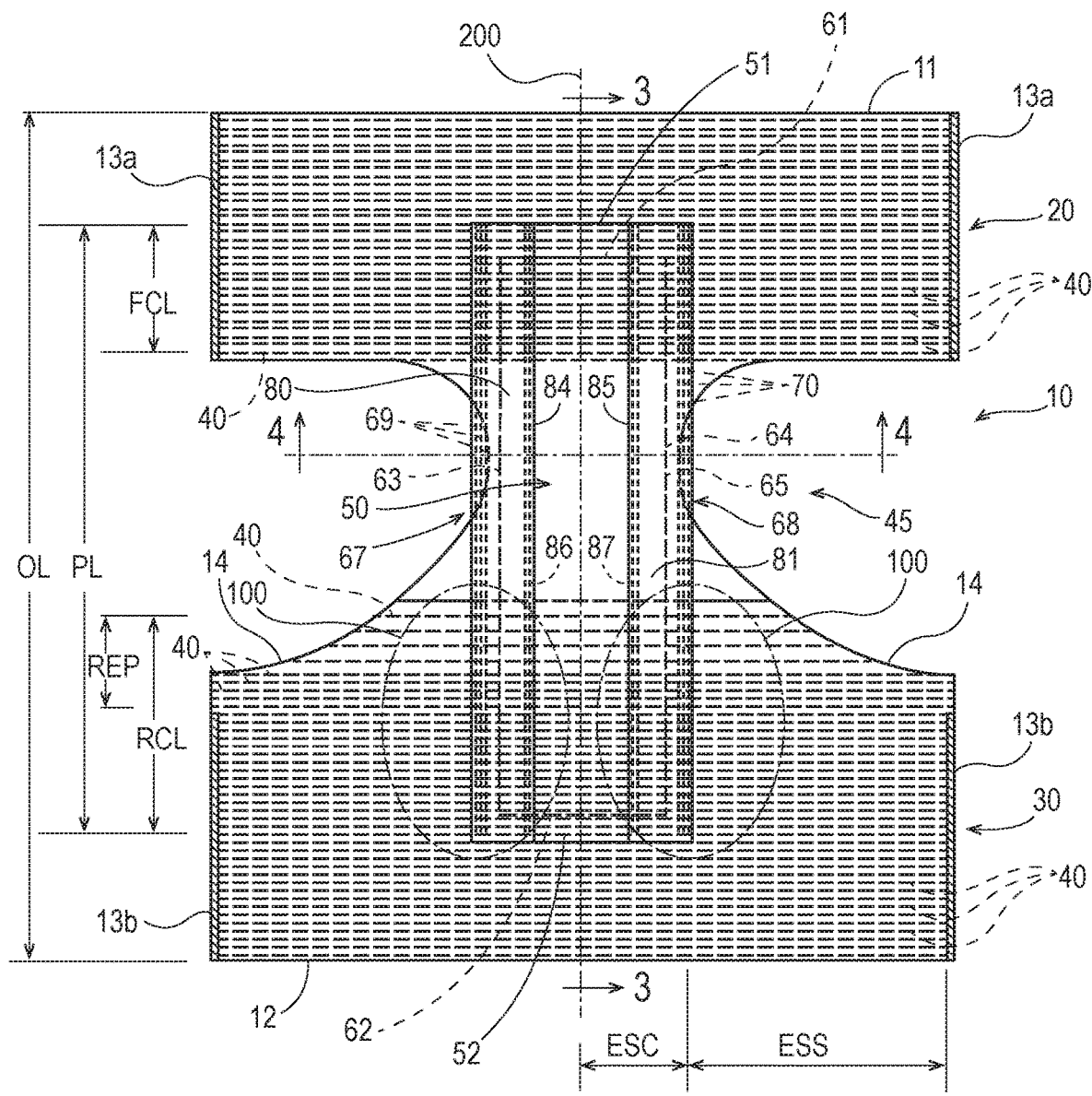
FIG. 2 is a schematic plan view of an example of a pant structure, depicted with the wearer-facing surfaces facing the viewer, with the front and rear panels separate (prior to attachment therebetween at side seams, or following separation at side seams) and with the structure in a flattened condition, stretched out to the full lengths and widths of the component materials against contraction induced by included elastomeric members.

"Above", when used to characterize the location of a second feature relative the location of a first feature of an assembled pant in a position such as depicted in FIG. 1, means that the second feature is longitudinally closer to the waist edges than the first feature. Conversely, in the same context, "below" means that the second feature is longitudinally closer to the lowermost extent of the crotch region than the first feature. "Above", when used to characterize the location of a second feature relative the location of a first feature of an opened, laid out pant structure in a position such as depicted in FIG. 2, means that the second feature is longitudinally closer to a waist edge than the first feature. Conversely, in the same context, "below" means that the second feature is longitudinally closer to the midpoint of the longitudinal axis than the first feature.

"Cross direction" (CD)—with respect to the making of a nonwoven web material, the nonwoven material itself, a laminate thereof, or an article in which the material is a component, refers to the direction along the material substantially perpendicular to the direction of forward travel of the material through the manufacturing line in which the material and/or article is manufactured.

Throughout the present description, a material or composite of materials is considered to be "elastic" or "elastomeric" if, when a biasing force is applied to the material, the material or composite can be extended to an elongated length of at least 150% of its original relaxed length (i.e. can extend at least 50%), without rupture or breakage which substantially damages the material or composite, and when the force is removed from the material or composite, the material or composite recovers at least 40% of such elongation. In various examples, when the force is removed from an elastically extensible material, the material or composite may recover at least 60% or even at least 80% of its elongation.

The "stretch direction" of a stretch laminate is the direction along which the laminate will most readily undergo elastic stretch and contraction. In a stretch laminate in which one or more elastic members are incorporated into the laminate while in a prestrained condition, the stretch direction is the direction along which the elastic member(s) are prestrained. The "trans-stretch direction" of a stretch laminate is the direction perpendicular to the stretch direction.

"Film" means a skin-like or membrane-like layer of material formed of one or more polymers, which does not have a form consisting predominately of a web-like structure of consolidated polymer fibers and/or other fibers.

"Lateral"—with respect to a pant and its wearer, refers to a direction generally perpendicular with the wearer's standing height, or the horizontal direction when the wearer is standing. With respect to a pant precursor structure such as depicted in FIG. 2, "lateral" refers to a direction substantially parallel with the waist edges 11, 12.

"Longitudinal"—with respect to a pant and its wearer, refers to the direction generally parallel with the wearer's standing height, or the vertical direction when the wearer is standing. With respect to a pant precursor structure such as depicted in FIG. 2, "longitudinal" refers to a direction substantially perpendicular to the waist edges 11, 12.

"Machine direction" (MD)—with respect to the making of a nonwoven web material, the nonwoven material itself, or a laminate thereof, refers to the direction along the material or laminate substantially parallel to the direction of forward travel of the material or laminate through the manufacturing line in which the material or laminate is manufactured.

A "nonwoven" is a manufactured sheet or web of directionally or randomly oriented fibers which are first laid down to form a batt and then consolidated and bonded together by friction, cohesion, adhesion or one or more patterns of bonds and bond impressions created through localized compression and/or application of pressure, heat, ultrasonic or heating energy, or a combination thereof. The term does not include fabrics that are woven, knitted, or stitch-bonded with yarns or filaments. The fibers may be of natural and/or man-made origin and may be staple and/or continuous filaments or be formed in situ. Commercially available fibers have diameters ranging from less than about 0.001 mm to more than about 0.2 mm and they come in several different forms: short fibers (known as staple, or chopped), continuous single fibers (filaments or monofilaments), untwisted bundles of continuous filaments (tow), and twisted bundles of continuous filaments (yarn). Nonwoven fabrics can be formed by many processes including but not limited to meltblowing, spunbonding, spunmelting, solvent spinning, electrospinning, carding, film fibrillation, melt-film fibrillation, airlaying, dry-laying, wetlaying with staple fibers, and combinations of these processes as known in the art. The basis weight of nonwoven fabrics is usually expressed in grams per square meter (gsm).

"z-direction," with respect to a nonwoven web, panel, or component of an absorbent core structure, means generally orthogonal or perpendicular to the planes approximated by the larger surfaces of the web, panel or component along the machine and cross direction dimensions.

Unless otherwise specified, all dimensions of a pant structure expressed herein (a non-limiting example of which is depicted in FIG. 2) are measured with the structure laid out flat, with non-elastic materials of the structure extended laterally and longitudinally to their full widths and lengths, against any contraction induced by the presence of pre-strained elastic strands or other elastic members.

Wherever a series of successively narrowing ranges of numbers or values for a variable feature are described, it is intended that the description contemplates any combination of the upper and lower limits of the ranges. For example, if a series of ranges is: "from 1 to 10, more preferably from 3 to 8," it is intended that the description also contemplates "from 1 to 8" and "from 3 to 10." This is not intended, however, to implicitly alter the meanings or limits of ranges as expressly set forth in the claims.

Description

General Pant Structure

FIG. 1 depicts an example of a belt- or balloon-type disposable absorbent pant 10. FIG. 2 depicts a pant structure shown with front 20 and rear 30 panels separated from the side seams 13, with the resulting structure laid out flat and stretched out to the fullest dimensions of the various components, against any contraction induced by included pre-strained elastic members. The pant 10 may have a waist opening defined by a front waist edge 11 and rear waist edge 12 and a pair of leg openings defined by respective leg opening edges 14. Pant 10 may include a belt structure having a front panel 20 and a rear panel 30, which are joined at seam areas 13a, 13b to form side seams 13 and complete the pant structure. Side seams 13 may be butt seams at which seam areas 13a, 13b proximate the side edges of front and rear panels 20, 30 are bonded together by any suitable bonding mechanism. A suitable bonding mechanism may include welding/thermal bonding, in which polymer materials in the front and rear panels 20, 30 are fused together by application of a combination of heat and pressure. Pant 10 may also include an absorbent pad assembly 50 overlying the front 20 and rear 30 panels to the insides thereof, and bridging them through a crotch region of the pant. Absorbent pad assembly 50 may be bonded to the inside surfaces of front and rear panels 20, 30 by any suitable bonding mechanism, such as a hot melt adhesive applied during the manufacturing process. When laid out as depicted in FIG. 2, the structure may be divided longitudinally in substantially mirror-image halves by a longitudinal axis 200.

Belt/Panel Structure

Figure 3:
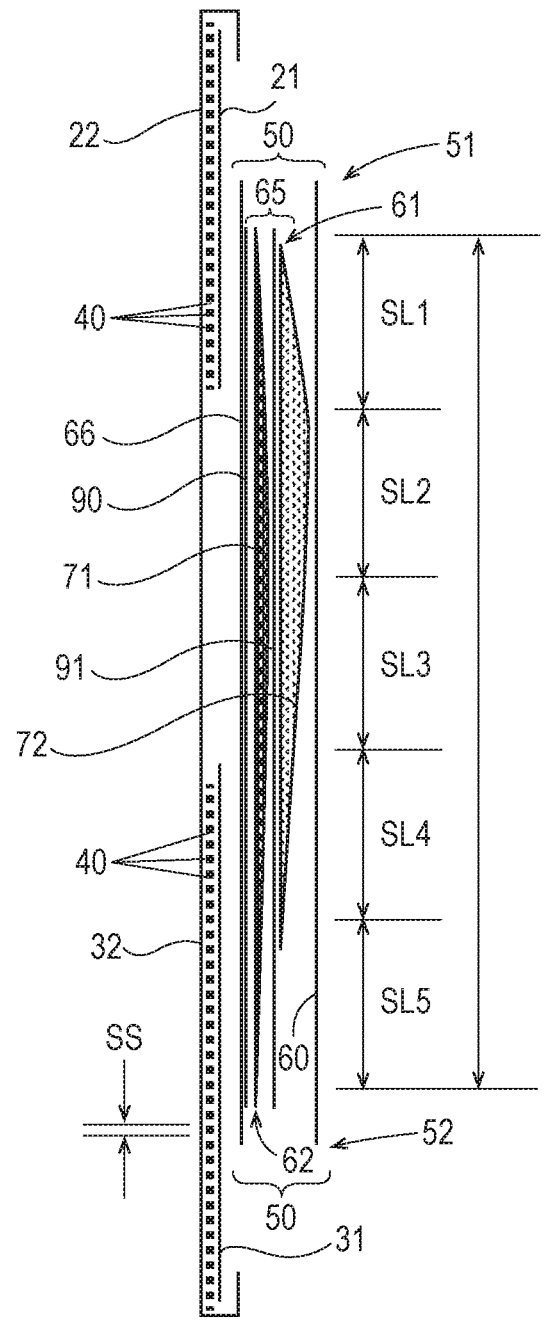
FIG. 3 is a schematic longitudinal cross-section view of the pant structure depicted in FIG. 2, taken along line 3-3 in FIG. 2.

Referring to FIGS. 2 and 3, pant 10 may include a belt structure including front panel 20 and rear panel 30. In the example depicted in FIGS. 2 and 3, outer layers 22, 32 of the front and rear panels are formed of a continuous layer common to both panels, which also wraps about the outside of the pant through the crotch region; this configuration is sometimes called a "unibody" construction. In another possible configuration (not shown), front 20 and rear 30 panels may have discrete, separate outer layers, have no layer in common, and be joined only by the side seams 13 and the absorbent pad assembly. This alternative configuration is sometimes called a "multipiece" construction.

In the example depicted, outer layers 22, 32 of respective front and rear panels 20, 30 may each be formed of a layer of nonwoven web material, which also may serve as the outer layer of the pant through the crotch region. Front and rear panels 20, 30 may also include inner layers 21, 31. Inner layers 21, 31 also may each be formed of layer(s) of nonwoven web material.

Suitable nonwoven web materials that may be useful as components to form the inner and outer layers 21, 31, 22, 32 of front and rear panels 20, 30 include, but are not limited to, spunbond, spunlaid, meltblown, spunmelt, solvent-spun, electrospun, carded, film fibrillated, melt-film fibrillated, air-laid, dry-laid, wet-laid staple fibers, and other nonwoven web materials formed in part or in whole of polymer fibers. The nonwoven web materials may be formed predominately of polymeric fibers. In some examples, suitable non-woven fiber materials may include, but are not limited to polymeric materials such as polyolefins, polyesters, polyamide, or specifically, polypropylene (PP), polyethylene (PE), polylactic acid (PLA), polyethylene terephthalate (PET) and/or blends thereof. In some examples, the fibers may be formed of PP/PE blends such as described in U.S. Pat. No. 5,266,392. Nonwoven fibers may be formed of, or may include as additives or modifiers, components such as aliphatic polyesters, thermoplastic polysaccharides, or other biopolymers. Further useful nonwovens, fiber compositions, formations of fibers and nonwovens and related methods are described in U.S. Pat. Nos. 6,645,569; 6,863,933 and 7,112,621; and in co-pending U.S. patent application Ser. Nos. 10/338,603; 10/338,610; and Ser. No. 13/005,237.

The individual fibers of the nonwoven web materials may be monocomponent or multicomponent. Multicomponent fibers may be bicomponent fibers, such as in a core-and-sheath or side-by-side arrangement. Often, the individual components comprise polyolefins such as polypropylene or polyethylene, or their copolymers, polyesters, thermoplastic polysaccharides or other biopolymers.

The nonwoven web material may provide good recovery when external pressure is applied and removed. The nonwoven web material may include a blend of different fibers selected, for example from the types of polymeric fibers described above. In some examples, at least a portion of the fibers may exhibit a spiral curl which has a helical shape. As noted, the fibers may include bicomponent fibers, which are individual fibers each comprising different materials, usually a first and a second polymeric material. It is believed that the use of side-by-side bi-component fibers is beneficial for imparting a spiral curl to the fibers.

In order to enhance tactile and/or visual perceptions of softness of a nonwoven web material, it may be treated by hydrojet impingement, which may also be known as hydroenhancement, hydroentanglement or hydroengorgement. Examples of such nonwoven web materials and processes are described in, for example, U.S. Pat. Nos. 6,632,385 and 6,803,103, and U.S. Pat. App. Pub. No. 2006/0057921.

Other examples of nonwoven web that may be useful may include an SMS web (spunbond-meltblown-spunbond web) made by Avgol Nonwovens LTD, Tel Aviv, Israel, under the designation XL-S70-26; an SSS (spunbond-spunbond-spunbond) web made by Pegas Nonwovens AS in Znojmo, Czech Republic, under the designation 18 XX 01 00 01 00 (where XX=the variable basis weight); an SSS web made by Gulsan Sentetik Dok San VE TIC AS, in Gaziantep, Turkey, under the designation SBXXFOYYY (where XX=the variable basis weight, and YYY=the variable cross direction width); an HESB (hydroenhanced spunbond) web made by First Quality Nonwovens Inc., in Hazelton, Pa., under the designation SEH2503XXX (where XXX=the variable cross direction width); and a bicomponent SS web.

A nonwoven web material useful as a component to form one or more of layers 21, 31, 22, 32 may be bonded in a pattern of bonds. A batt of loose, e.g., spunlaid, fibers may be passed through the nip between a pair of calender bonding rollers and thereby consolidated and bonded in a pattern of bonds, to add machine- and cross-direction tensile strength and dimensional stability, converting the batt of loose fibers to a coherent and useable nonwoven web material. The bonding may include a pattern of thermal bonds, mechanical bonds, adhesive bonds or a combination thereof, although in some circumstances thermal bonding may be preferred. Thermal bonds may be formed by supplying one or both of the calender rollers or accompanying equipment with a source of heating energy that functions to heat the fibers and cause them to melt and fuse beneath bonding projections in the nip between the calender bonding rollers. One or both of the rollers may be machined, etched or otherwise formed to have a pattern of shaped bonding projections extending radially outward from the cylindrical surface of the roller. When the rollers are maintained in suitably close proximity with their axes in parallel, the batt of fibers passing therebetween will be subjected to pressure concentrated in the nip beneath the bonding projections, and fibers passing through the nip and beneath the bonding projections will be deformed and at least partially fused (by application of heating energy), to form bonds. Each bond will have a shape, and the bonds will have a pattern and spacing, substantially corresponding to the shape, pattern and spacing of the bonding projections on the calender bonding roller.

In some examples, a pattern of thermal bonds used to bond nonwoven web materials used to form one or more of layers 21, 31, 22, 32 may have features described in U.S. Prov. Pat. App. Ser. No. 62/331,650.

Referring to FIGS. 2 and 3, layers 21, 31, 22, 32 of either or both of front and rear panels 20, 30 may sandwich one or more elastic members, such as a plurality of laterally extending strands 40 of an elastomeric material, such as an elastane (for example, LYCRA HYFIT fiber, a product of Invista, Wichita, Kans.). Layers 21, 31, 22, 32 may respectively be joined together about elastic strands 40 by adhesive deposited between the layers, by thermal bonds, by compression bonds, or by a combination thereof. In other examples, the one or more elastic members may be strips or a section of film formed of elastomeric material. Elastic strands rather than film, however, may be preferred for the flexibility they provide by enabling individualized setting of prestrain levels, selecting and setting uniform or varying longitudinal spacing therebetween, and preserving a high level of vapor transmission (breathability) through the belt laminate, for purposes of coolness, comfort and skin health. This flexibility helps enable the manufacturer to enhance the fit of the pant structure about the varying contours and sizes of differing wearers' anatomies, and impart a cloth-like appearance to the belt laminate. (For purposes herein, a "strand" is a member having a cross section perpendicular to its longest dimension, the cross section having an aspect ratio of largest dimension to smallest dimension no greater than 2, in an unstrained condition.)

The elastic members can also be formed from various other materials, such as but not limited to, rubbers, styrene ethylbutylene styrene, styrene ethylene propylene styrene, styrene ethylene propylene styrene, styrene butadiene styrene, styrene isoprene styrene, polyolefin elastomers, elastomeric polyurethanes, and other elastomeric materials known in the art, and combinations thereof. In some embodiments, the elastic members can be extruded strand elastics with any number of strands (or filaments).

Elastic strands, if used, may be selected to have a decitex ranging from 50 to 2000, or any integer value for any decitex value in this range, or any range formed by any of these integer values. For purposes herein, however, it may be preferred that elastic strands included to elasticize the major portions of the front and/or rear panels 20, 30 above the bottoms of the side seams 13 have a decitex of from 400 to 1000, more preferably 500 to 900, and still more preferably 600 to 800. In one example, a waistband region of a panel (the region immediately below the waist edge 11 or 12 of the panel) may include from 3 to 12 elastic strands having a higher decitex, and a plurality of strands below the waistband region having a lower decitex. In a more particular example, a waistband region of a pant may include from 3 to 12, more preferably from 4 to 10, and still more preferably from 5 to 10, elastomeric strands having a decitex of from 400 to 1000, more preferably 500 to 900, and still more preferably 600 to 800, and a plurality of strands below the waistband region and above the bottom ends of side seams 13 having a decitex of 300 to 680, more preferably 400 to 580. Use of higher decitex elastomeric strands in a waistband region can be used to provide the pant with relatively greater tension in that region than in lower regions, providing a pant that holds securely and comfortably to the wearer's body about the waistband.

Alternatively, the elastic members may be one or more sections or strips of elastomeric film. Examples of elastomeric films have been described extensively in prior patent applications (see, for example, U.S. Pat. App. Pub. No. 2010/0040826). The film may be created with a variety of resins combined in at least one of several sublayers, the latter providing different benefits to the film. Elastic members may also be in the form of scrim, strips or sections of tape of elastomeric material with their longer dimensions oriented along the stretch direction.

During manufacture of the belt structure, the one or more elastic members such as elastic strands 40, may be prestrained lengthwise (along the lateral direction) by a desired amount as they are being incorporated into the belt structure. Upon subsequent relaxation of the belt, the one or more elastic members, such as elastic strands 40, will contract toward their unstrained lengths. This causes the sandwiching layers 21, 22 and/or 31, 32 to gather and form ruffles or gathers having ridges and valleys extending generally transversely to the lengths of the elastic strands 40 (i.e., in a longitudinal direction), and also extending in the z-direction. The direction of prestrain corresponds with the stretch direction of the laminate. For purposes herein, and in combination with other features described herein, it may preferred that strand elastic members 40 in the front and/or rear panels 20, 30, be prestrained during manufacture by an amount of from 50% to 290%, more preferably from 90% to 230%, and still more preferably from 120% to 180%, and be affixed between the inner and outer layers of the panels while in such prestrained condition. (Herein, the amount of prestrain of an elastic strand member is expressed as [((prestrained unit length)−(unstrained unit length))/(unstrained unit length)]×100%. For example, a unit length of elastic strand prestrained to twice its unstrained length has a prestrain of 100%.) In combination with one or more of the decitex and strand spacing features described herein, a prestrain level within this range is believed to balance belt structure comfort, close fit, appropriate lateral tension, smoothly distributed over the longitudinal dimension of the belt for causing the absorbent pad assembly to hug the wearer's body, and a cloth-like appearance resulting from the many relatively controlled, small ridges and valleys of ruffles/gathers in the material resulting from prestrain in the elastic strand members.

In the more particular example having waistband region elastic members of differing decitex than those below the waistband region, described above, the waistband region elastic members may be prestrained during manufacture by an amount of from 110% to 350%, more preferably from 150% to 290%, and still more preferably from 180% to 240%, while the elastic members below the waistband region may be prestrained during manufacture an amount of from 50% to 290%, more preferably from 90% to 230%, and still more preferably from 120% to 180%.

Where prestrain level for an elastic member is not included in the manufacturer's specifications, it can be calculated, or empirically determined, from known or readily determinable stretch/strain properties of the member and from the level of tensile force introduced into the member as it is incorporated into the belt structure laminate. Alternatively, the amount of prestrain can be measured by making products on the production line with adhesive deposition apparatus turned off for selected samples of the elastic members, and then measuring the stretched and relaxed lengths of the members in the unadhered regions.

The size(s) and shape(s) of the ruffles or gathers may be affected, and may be manipulated, by design of the pattern of joined portions and/or bonding between respective pairs of layers 21, 22 and 31, 32, with respect to each other and with respect to elastic strands 40. The size(s) and shape(s) may also depend upon, and be manipulated by, the selected longitudinal spacing SS of the elastic strands.

As noted, in one example, a stretch laminate may be elasticized by incorporated elastic strands 40 as the elastic stretch mechanism. Elastic strands 40 may have adhesive applied to them prior to lamination (e.g., by a strand coating process), such that, when the web layers 21, 22 and/or 31, 32 are brought together to sandwich the strands, the applied adhesive causes the web layers to be adhered about the strands to form the stretch laminate. The adhesive applied to the elastic strands may be the only adhesive used to hold the laminate together. This configuration helps keep the strands secured between the layers in their longitudinal positions, while allowing the layer materials between the strands to move freely with respect to each other, providing for even formation of gathers/ruffles, and superior breathability. Alternatively, or in addition, adhesive may be deposited upon one or both layers 21, 22 and/or 31, 32 prior to lamination, and may be deposited in a pattern. Examples of methods for applying patterned deposits of adhesive to a nonwoven web substrate to enable manufacture of an elasticized laminate are described in U.S. Pat. No. 8,186,296. In one example, the adhesive pattern selected may be effected by design of a correspondingly designed roller. The pattern of adhesive to be applied may be designed to affect the size(s) and shape(s) of the ruffles or gathers. The layers 21, 22 and/or 31, 32 may be adhesively joined and/or bonded to each other at the locations of adhesive deposits, and remain unjoined or unbonded, or free, of each other at other locations, such that they may move and shift slightly relative each other as the laminate is moved and stretched, as during wear of the article.

Various coating methods and techniques, including strand coating methods and techniques, are shown for example in U.S. Pat. Nos. 5,340,648; 5,501,756; 5,507,909; 6,077,375; 6,200,635; 6,235,137; 6,361,634; 6,561,430; 6,520,237; 6,582,518; 6,610,161; 6,613,146, 6,652,693, 6,719,846 and 6,737,102. The adhesive used may be a hot-melt type adhesive having elasticity and flexibility making it suitable for attaching prestrained elastic materials to substrates, such as OMNIMELT BLOCKS 22 H2401F, or ZEROCREEP brands such as AVANCE, available from Bostik, Inc., Wauwatosa, Wis.

When bonding of one or both of nonwoven layers 21, 22 and/or 31, 32 is effected using thermal calender bonding, the joining and/or bonding pattern may be designed to affect the size(s) and shapes of the ruffles or gathers. It may be desired in some circumstances that a spunlaid nonwoven web be bonded with a pattern of thermal bonds to a bond area of from 5% to 20%. For purposes described herein it may be desired that bond area be from 8% to 15%. Patterned thermal bonding tends to enhance machine-direction and cross-direction strength and dimensional stability of the resulting bonded nonwoven web, which has benefits in downstream converting and processing operations, and adds tensile strength and robustness to a product in which the web is to form a component. However, thermal bonding also generally increases the stiffness of the resulting bonded nonwoven web. This may have adverse effects on the product consumer's perception of tactile softness of the product surfaces. For example, if the web is used as a layer of a belt structure of a pant product, stiffness imparted to the web may cause the consumer to negatively perceive the belt layer as stiff- or rough-feeling. For this reason, in some circumstances it may be desired to limit bond area to less than 16%, less than 12%, or even less than 10%. Further, imparting certain additional features described in U.S. Prov. Pat. App. Ser. No. 62/331,650 to the bond pattern of a web to be used in a stretch laminate can mitigate the negative effects of stiffening the web, while providing advantages in addition to tensile strength. As disclosed in the above-cited '650 application, nonwoven web material bond patterns having a majority of bonding shapes in the pattern that that are longer in the cross direction than in the machine direction of the nonwoven web may tend to form more controlled, smaller ruffles or gathers, making the belt laminate more cloth-like in appearance.

For purposes of reducing the overall size of the ruffles or gathers formed, and in conjunction with any combination of the features described herein, it may be desired that the average longitudinal spacing SS between subsets of, or all of, the elastic strands 40 above the bottoms of side seams 13 be no greater than 14 mm, more preferably no greater than 10 mm, even more preferably no greater than 7 mm, and still more preferably no greater than 5 mm. (Herein, longitudinal spacing between adjacent elastic strands is to be understood to refer to the distance between their axes, not the distance between their nearest outer surfaces.) Through experimentation it has been determined that limiting spacing of elastic strands 40 in this way has the effect of promoting formation of ruffles or gathers that of a controlled small size, thereby providing or enhancing a cloth-like appearance in the stretch laminate.

Absorbent Pad Assembly

Absorbent pad assembly 50 may include any combination of components found in disposable diapers and absorbent pants, including but not limited to a liquid impermeable backsheet, a liquid permeable topsheet, an absorbent core structure disposed between the topsheet and backsheet, and elasticized barrier cuffs. Examples and descriptions of components and configurations of such an absorbent pad assembly or central chassis may be found in U.S. patent application Ser. No. 13/764,945, wherein the chassis described includes components and features that may be included. As described herein, additional features and combinations thereof may be included as well.

Referring to FIGS. 2, 3 and 4A-4C, absorbent pad assembly 50 has a front end 51, rear end 52, left edge 67 and right edge 68. Assembly 50 may include a liquid permeable topsheet 60, a liquid impermeable backsheet 66, and an absorbent core structure 65 disposed between the topsheet and backsheet. The topsheet 60 may be formed of a nonwoven web material suitably selected to contain the components of the absorbent core structure while permitting urine to freely pass therethrough, from the wearer-facing surface to the absorbent core structure 65. The backsheet 66 may include or be formed at least in part of a polymeric film material suitably selected to contain the components of the absorbent core structure, and also to contain and prevent passage of urine from the absorbent core structure therethrough, to the outward-facing surface, under ordinary conditions of use. In some examples the backsheet 66 may also include an outer layer formed of a nonwoven web material to provide added strength and impart a more cloth-like feel. In some examples the backsheet film may be formed so as to be breathable, such that it can permit water vapor to pass therethrough, while still preventing aqueous liquid (urine) from passing therethrough, which can help improve comfort of the pant for the wearer. Materials for suitable topsheet and backsheet materials are well-known in the art. The materials of the topsheet and backsheet may be joined and bonded together about their peripheries, to form an envelope structure containing the absorbent core structure 65, by any suitable bonding mechanism, for example, hot melt adhesive.

The absorbent pad assembly 50 may include a pair of longitudinal barrier cuffs 80, 81, with respective proximal portions 82, 83 attached to the assembly, and respective free edges 84, 85 that are free to extend away from the assembly and toward the wearer, when the assembly curves about the wearer's body through the crotch region the free edges are pulled longitudinally taut by barrier cuff edge elastic members 86, 87. Barrier cuff edge elastic members 86, 87 may be incorporated into the cuff structures while in a prestrained condition, which will cause the free edges to be in longitudinal tension and tend to gather to cause the edges to extend away from the assembly and conform to the wearer's body contours when the pant is worn. The barrier cuffs may be formed of an effectively liquid impermeable material, such as a film material or a breathable but effectively liquid impermeable nonwoven web material, and may serve to contain discharges of urine within the pant prior to its absorption by the absorbent core structure. The pad assembly 50 also may include longitudinal edge elastic members 69, 70, which also may be incorporated into the assembly while in a prestrained condition, which will cause the longitudinal left and right edges 67, 68 of the assembly to gather about the wearer's legs through the crotch region, furthering the containment function and enhancing fit. Longitudinal edge elastic members 69, 70 may be disposed between the materials of the barrier cuffs 80, 81 and topsheet 60 as shown in the figures. Alternatively, they may be disposed between the topsheet and backsheet, or outside of the outward-facing side of the backsheet.

Barrier cuffs and associated longitudinal edge structures and elastic members may also be formed of materials and configured as described in any of, for example, U.S. Pat. No. 8,939,957; US2016/270978; US2016/270971; US2016/270980; US2016/270985; US2016/270983; US2016/270979; US2016/270975; US2016/270981, and US2016/270973.

Longitudinal edge elastic members 69, 70, and barrier cuff edge elastic members 86, 87 may be elastic strands, preferably of the same material as that of elastic strands 40 in the panels 20, 30. Some or all of elastic members 69, 70, 86, 87 also may be selected as to have a decitex of from 400 to 1000, more preferably 500 to 900, and still more preferably 600 to 800, and most preferably the same decitex as that of the elastic strands 40 of panels 20, 30 in the waistband region. Elastic members 69, 70, 86, 87 may also be incorporated into the structure prestrained by an amount of from 50% to 290%, more preferably from 90% to 230%, and still more preferably from 120% to 180%, and preferably by an amount that is the same or more than the prestrain amount of that of the elastic strands 40 (below the waistband region), and be affixed within the absorbent pad assembly while in such prestrained condition. Incorporating elastic strands of size and prestrain levels for longitudinal edge elastic members 69, 70, and/or barrier cuff edge elastic members 86, 87, as those of panel elastic strands 40, limited as described above, may help prevent visibly obvious and/or excessive distortion of the otherwise smooth outward appearance of the panels 20, 30, that may be caused by inclusion of longitudinally oriented elastic members with disproportionately greater levels of tension therein, pulling longitudinally on the panels from the insides thereof.

FIGS. 3 and 4A-4C are schematic, exploded-view depictions of cross-sections shown with the depicted components separated from each other. It will be appreciated, however, that the materials depicted may be bonded together to form the pant assembly by any suitable mechanism, for example, by thermal bonding, or by hot melt adhesive deposited between the respective components to be bonded. For the example, the materials of the topsheet 60 and backsheet 66 may be bonded together about their perimeters to form an envelope structure that contains the absorbent core structure 65. Similarly the proximal portions 82, 83 of barrier cuffs 80, 81 may be bonded to the topsheet or other portion of the assembly by any suitable mechanism such as hot melt adhesive.

Absorbent Core Structure

The absorbent core structure 65 will have a front edge 61, rear edge 62, leftmost edge 63 and rightmost edge 64. The absorbent core structure 65 may include one or more layers that serve differing liquid-handling and storage functions. In the example depicted in the figures, absorbent core structure 65 may include an absorbent layer 71 and an acquisition layer 72. Absorbent layer 71 may be formed of an absorbent material that tends to attract and retain aqueous liquid such as urine. In some examples, absorbent layer 71 may include a distribution of particles of absorbent gel material (AGM), also known as superabsorbent polymer (SAP).

Figure 4A:
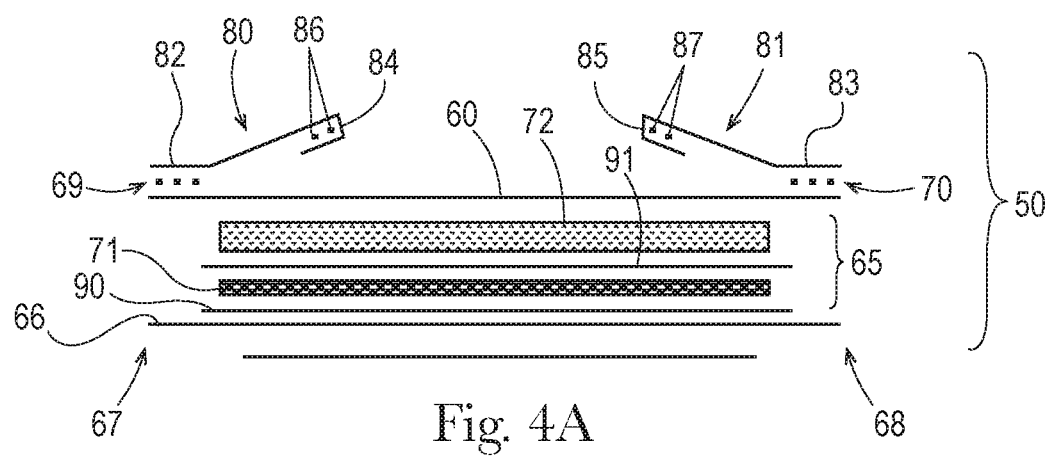
FIG. 4A is a schematic lateral cross-section view of one alternative example of the pant structure depicted in FIG. 2, taken along line 4-4 in FIG. 2.
Figure 4B:
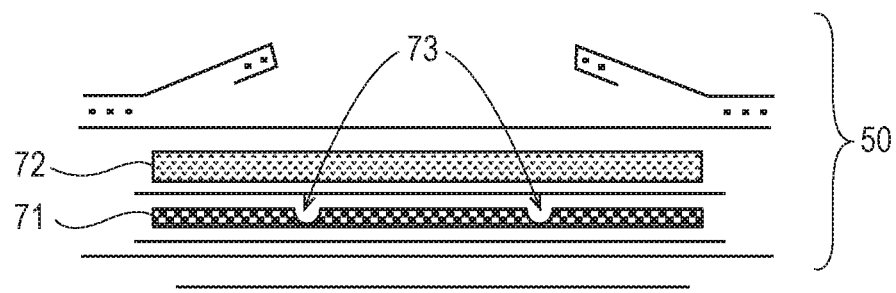
FIG. 4B is a schematic lateral cross-section view of another alternative example of the pant structure depicted in FIG. 2, taken along line 4-4 in FIG. 2.
Figure 4C:
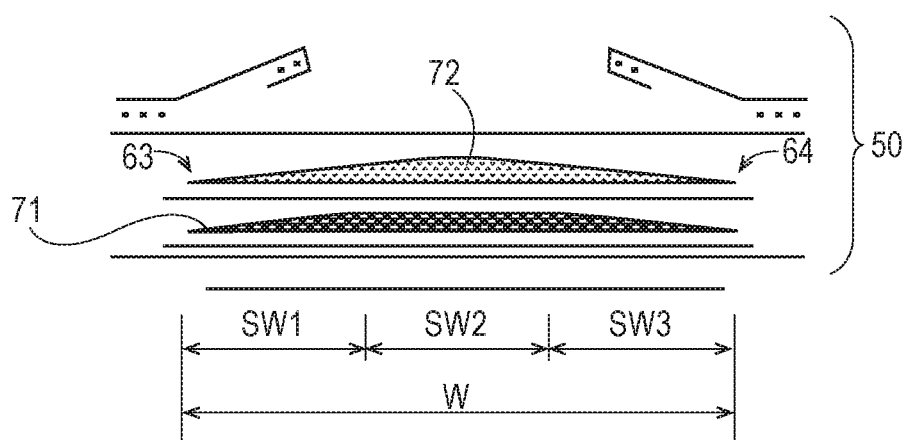
FIG. 4C is a schematic lateral cross-section view of another alternative example of the pant structure depicted in FIG. 2, taken along line 4-4 in FIG. 2.

The absorbent core structure 65 may include a substrate layer 90, and absorbent layer 71 may include superabsorbent polymer particles, and optionally cellulose fibers, supported by, and immobilized on, the substrate layer 90. Examples of absorbent core structures 65 are illustrated in FIGS. 4A-4C. The substrate layer 90 of the absorbent core structure may be any material capable of supporting the superabsorbent polymer particles. It may be a web or sheet material, such as foam, film, woven and/or nonwoven material. The substrate layer 90 and the absorbent layer 71 may be coextensive, or the substrate layer 90 may be slightly longer and wider than the absorbent layer 71.

As noted, the absorbent layer 71 may include superabsorbent polymer particles, and optionally cellulose fibers. The absorbent layer may include superabsorbent polymer in other forms such as superabsorbent polymer fibers. Superabsorbent polymer particles will be described in further detail below. The superabsorbent polymer particles may be used alone or in combination with other materials. In some examples, the absorbent layer includes superabsorbent polymer particles physically blended with cellulose fibers. "Cellulose" as used herein includes cellulose pulp fibers as well as comminuted wood pulp in the form of fibers, sometimes also referred in the art as "air-felt". In some examples, the absorbent layer includes more than 70%, or more than 80%, or more than 90%, or more than 95% or even 100% by weight of superabsorbent polymer particles. In some other examples, the absorbent layer includes superabsorbent polymer particles and less than 5% by weight of cellulose, or less than 2% by weight of cellulose, or even substantially no cellulose. In examples wherein the absorbent layer is cellulose free, the only absorbent material in the absorbent layer is the superabsorbent polymer (particles, fibers, etc.). The resulting absorbent core structures have a reduced thickness in the dry state compared to conventional absorbent core structure including cellulose fibers. The reduced thickness reduces overall bulk of the pant and helps to improve the fit and comfort of the pant for the wearer.

The superabsorbent polymer particles may be immobilized on a substrate layer by, for example, a thermoplastic adhesive material.

"Superabsorbent polymer" (or "SAP") as used herein refers to absorbent materials which are cross-linked polymeric materials that can absorb at least 10 times their weight of an aqueous 0.9% saline solution as measured using the Centrifuge Retention Capacity (CRC) test (EDANA method WSP 241.2-05E). The SAP used may in particular have a CRC value of more than 20 g/g, or more than 24 g/g, or of from 20 to 50 g/g, or from 20 to 40 g/g, or from 24 to 30 g/g. The SAP useful in the present invention include a variety of water-insoluble, but water-swellable polymers capable of absorbing large quantities of fluids.

The superabsorbent polymer can be in particulate form so as to be flowable in the dry state. Typical particulate superabsorbent polymer materials are made of poly(meth)acrylic acid polymers. However, e.g. starch-based particulate superabsorbent polymer material may also be used, as well polyacrylamide copolymer, ethylene maleic anhydride copolymer, cross-linked carboxymethylcellulose, polyvinyl alcohol copolymers, cross-linked polyethylene oxide, and starch grafted copolymer of polyacrylonitrile. The superabsorbent polymer may be polyacrylates and polyacrylic acid polymers that are internally and/or surface cross-linked. Suitable materials are described in, for example, PCT Patent Applications Nos. WO07/047598, WO07/046052, WO2009/155265 and WO2009/155264. In some embodiments, suitable superabsorbent polymer particles may be obtained by current state of the art production processes as is more particularly as described in WO2006/083584. The superabsorbent polymers are preferably internally cross-linked, i.e., the polymerization is carried out in the presence of compounds having two or more polymerizable groups which can be free-radically copolymerized into the polymer network. Useful crosslinkers include for example ethylene glycol dimethacrylate, diethylene glycol diacrylate, allyl methacrylate, trimethylolpropane triacrylate, triallylamine, tetraallyloxyethane as described in EP0530438, di- and triacrylates, as described in EP0547847, EP0559476, EP0632068, WO93/21237, WO03/104299, WO03/104300, WO03/104301 and in DE10331450, mixed acrylates which, as well as acrylate groups, include further ethylenically unsaturated groups, as described in DE10331456 and DE10355401, or crosslinker mixtures as described for example in DE19543368, DE19646484, WO90/15830 and WO02/32962 as well as cross-linkers described in WO2009/155265. The superabsorbent polymer particles may be externally surface cross-linked, or post cross-linked). Useful post-crosslinkers include compounds including two or more groups capable of forming covalent bonds with the carboxylate groups of the polymers. Useful compounds include for example alkoxysilyl compounds, polyaziridines, polyamines, polyamidoamines, di- or polyglycidyl compounds as described in EP0083022, EP0543303 and EP0937736, polyhydric alcohols as described in DE-C3314019, cyclic carbonates as described in DE-A4020780, 2 oxazolidone and its derivatives, such as N-(2-hydroxyethyl)-2-oxazolidone as described in DE-A19807502, bis- and poly-2-oxazolidones as described in DE-A19807992, 2-oxotetrahydro-1,3-oxazine and its derivatives as described in DE-A19854573, N-acyl-2-oxazolidones as described in DE-A19854574, cyclic ureas as described in DE-A10204937, bicyclic amide acetals as described in DE-A10334584, oxetane and cyclic ureas as described in EP1199327 and morpholine-2,3-dione and its derivatives as described in WO03/031482.

The SAP may be formed from polyacrylic acid/polyacrylate polymers, for example having a neutralization degree of from 60% to 90%, or about 75%, having for example sodium counter ions. Suitable SAP may also for example be obtained from inverse phase suspension polymerizations as described in U.S. Pat. Nos. 4,340,706 and 5,849,816 or from spray- or other gas-phase dispersion polymerizations as described in US2009/0192035, US2009/0258994 and US2010/0068520. In some embodiments, suitable SAP may be obtained by current state of the art production processes as is more particularly described from page 12, line 23 to page 20, line 27 of WO2006/083584.

The absorbent layer 71 may include only one type of SAP, but it may also include a blend of differing types or compositions of SAPs. The fluid permeability of a superabsorbent polymer can be quantified using its Urine Permeability Measurement (UPM) value, as measured in the test disclosed European patent application number EP12174117.7. The UPM of the SAP may for example be of at least $10 \times 10^{-7}$ cm3·sec/g, or at least $30 \times 10^{-7}$ cm3·sec/g, or at least $50 \times 10^{-7}$ cm3·sec/g, or more, e.g. at least 80 or $100 \times 10^{-7}$ cm3·sec/g. The flow characteristics can also be adjusted by varying the quantity and distribution of the SAP used in the absorbent core.

The superabsorbent polymer particles may be spherical, spherical-like, ellipsoid, or irregularly shaped, such as ovoid-shaped particles of the kind that may be obtained from inverse phase suspension polymerizations. The particles may, optionally, be agglomerated at least to some extent to form larger irregular agglomerations of particles.

In some examples, the absorbent layer may be substantially cellulose-free. Airfelt and other cellulose fiber have been used as absorbent fillers in absorbent cores of disposable diapers. Such fiber also has absorbent properties and imparts some absorption capacity to an absorbent layer, but also may be included to provide a structural matrix to hold dispersed particles of superabsorbent polymer particles. While inclusion of such particles enhances absorption capacity, keeping such particles suitably dispersed may be important to prevent the particles from "gel-blocking" in use as they swell with absorbed liquid and block the passageways therebetween which allow liquid to move through deposits thereof, compromising absorption capacity. The inclusion of airfelt or other cellulose fiber as a matrix for superabsorbent polymer particles can serve to reduce or prevent gel-blocking. However, it also imparts bulk to an absorbent layer, even before absorption of any liquids. To reduce the overall size and/or thickness of the absorbent layer, and thereby improve wearer comfort and reduce the bulkiness of the pant for purposes of packaging and shipping volume efficiency, it may be desired to construct an absorbent core using the lowest volumes of core materials possible within performance constraints. Toward this end, examples of suitable materials and constructions for a suitable absorbent core structure are described in, but are not limited to, U.S. patent application Ser. Nos. 12/141,122; 12/141,124; 12/141,126; 12/141,128; 12/141,130; 12/141,132; 12/141,134; 12/141,141; 12/141,143; and Ser. No. 12/141,146; and WO2008/155699. Generally, these applications describe absorbent layer constructions that minimize or eliminate the need for and inclusion of airfelt or other forms of cellulose fiber in combination with particles of superabsorbent polymer particles ("substantially cellulose-free" structures). Suitable methods for forming deposits of superabsorbent polymer particles are additionally disclosed in, for example, EP1621167A2, EP1913914A2 and EP2238953A2.

The superabsorbent polymer particles may be distributed and immobilized on the substrate layer. Immobilization may be achieved by applying a thermoplastic adhesive material, which holds and immobilizes the superabsorbent polymer particles, and cellulose when present, on the substrate layer. Some thermoplastic adhesive material may also penetrate into the layer of superabsorbent polymer particles and into the substrate layer to provide further immobilization and affixation. The thermoplastic adhesive material may not only help in immobilizing the superabsorbent polymer particles on the substrate layer but also may help in maintaining the integrity of any included channels (described further below). The thermoplastic adhesive material can help prevent a significant quantity of superabsorbent polymer particles from migrating into the channels.

Thermoplastic adhesive materials suitable for use in the present disclosure includes hot melt adhesives including at least a thermoplastic polymer in combination with a plasticizer and other thermoplastic diluents such as tackifying resins and additives such as antioxidants. Example suitable hot melt adhesive materials are described in EP1447067 A2.

Figure 5:
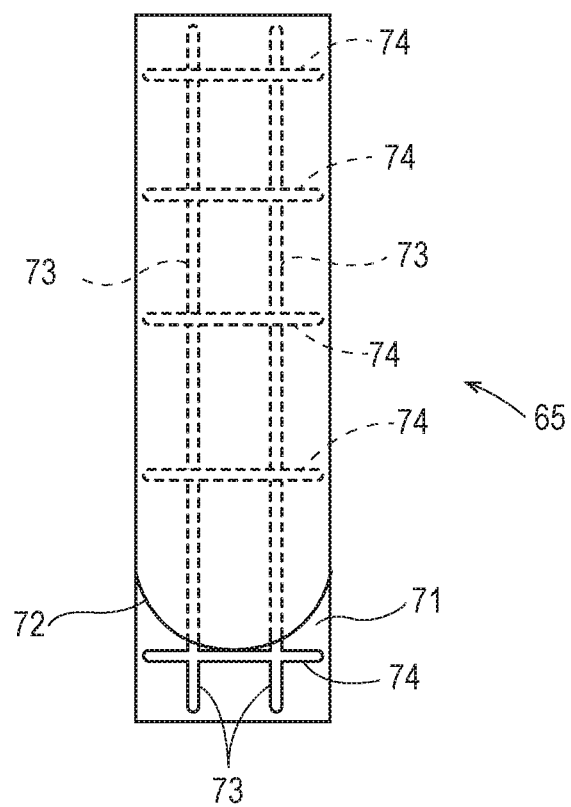
FIG. 5 is a schematic plan view of an absorbent core structure.

In some examples, as suggested in FIG. 5, in order to reduce the risk of urine leakage and/or runoff, it may be desired that any longitudinal channels 73 included do not extend all of the way to one or both of the front and rear edges 61, 62 of the absorbent core structure 65 or absorbent layer 71. The absorbent layer 71 may include, along each transverse edge and adjacent to said edge, an end deposit of superabsorbent polymer particles free of channels which extends in the transverse dimension of the absorbent layer from the leftmost edge 63 of the absorbent layer 71, to the rightmost edge 64. Similarly, it may be desired that any lateral channels 74 do not extend to the leftmost and rightmost edges 63, 64 of the absorbent core structure 65 and/or absorbent layer 71. The absorbent layer 71 may include, along each longitudinal edge, a side deposit of superabsorbent polymer particles free of channels, which extends the length of the absorbent layer 71 from the front edge 61 to the rear edge 62.

Referring to FIGS. 4B and 5, the absorbent layer 71 may include a plurality of longitudinal and/or lateral channels 73, 74. "Channels" as used herein refers to troughs or other identifiable elongate passageways formed through the deposit of superabsorbent polymer particles of the absorbent layer 71, partially or entirely extending through the z-direction thickness of the absorbent layer 71 and characterized by areas of comparatively reduced mass per unit spatial volume density of superabsorbent polymer particles in the space occupied by the absorbent core structure, or even by areas that are substantially free of superabsorbent polymer particles, i.e. substantially no superabsorbent polymer particles are present in such volume (longitudinal channel or lateral channel) of an absorbent core structure. The channels may substantially straight as depicted, or may be curved. The channels may have an average width of at least 3 mm (the average width of a channel is defined as the average distance between its longer boundaries).

The channels may be permanent. By permanent, it is meant that the integrity of the channels is substantially maintained both in dry state and wet state, i.e. the channels are substantially resistant to the effects of wetting (e.g., structure is maintained by materials that are insoluble in water), and substantially withstand mechanical stresses in the materials caused by swelling of superabsorbent polymer particles, pressure within the structure resulting therefrom, and the wearer's body movements. Permanent channels may be formed by immobilizing the superabsorbent polymer particles on the substrate layer, such as by applying a thermoplastic adhesive material over the absorbent layer. The absorbent layer of the present disclosure may also include permanent channels formed by permanently bonding of a first substrate layer 90 and a second substrate layer 91 together along the channels, thereby, in one example, forming chambers that separately envelope and contain superabsorbent polymer particle deposits and thereby define the channels therethrough. Adhesive may be used to bond the substrate layers 90, 91 together along the channels, but it is possible to bond the substrate layers together via other means, for example, ultrasonic bonding, pressure bonding or thermal bonding. The supporting layers may be continuously bonded or intermittently bonded along the channels.

As shown in FIGS. 4B and 5, the absorbent layer 71 may have two longitudinal channels 73 therethrough, such that the absorbent layer is divided longitudinally by the channels into three sections, at least in the crotch region of the absorbent pad assembly. In some examples, the two channels may extend longitudinally along at least 15%, or at least 20% or at least 30% and up to 50%, or up to 70% or up 90% of the length of the absorbent layer 71. In some examples, the longitudinal channels may be present only in the crotch region, and not in regions proximate front and rear edges 61, 62. When present only in the crotch region, the channels may extend over the whole longitudinal dimension of the crotch region, e.g. about 50% of the length of the absorbent layer, or they may extend in only part of the crotch region, i.e. from at least 15%, or at least 20% or at least 30% to 40%, or to 45% or to less than 50% of the length of the absorbent layer. In some examples, the longitudinal channels 73 may be present in the crotch region, or part thereof, and part of the front region and/or part of the back region (such as shown in FIG. 5). In some examples, the channels may be present in the front and crotch regions, i.e. the channels may extend from the crotch region (or part thereof) into the front region. In some examples, the channels may be present in the back and crotch regions, i.e. the channels extend from the crotch region (or part thereof) into the back region. The longitudinal channels 73 may be mirror images of one another with respect to the longitudinal axis 200 of the pant, i.e. the channel in a left longitudinal region may be mirror image of the channel in a right longitudinal region of the absorbent layer 71.

The longitudinal channels 73 may be substantially straight, and may run substantially parallel to the longitudinal axis 200 of the pant (shown in FIG. 2). Straight channels may serve as hinge structures in the absorbent core structure, which may help enable the absorbent core structure to flex laterally about the channels 73 and thereby better conform to the wearer's anatomy along the lateral direction through the crotch region, and may also help enable the absorbent core structure to form a containing shape better suited to receiving and containing liquid exudate before it is completely absorbed, when the pant is worn. Longitudinally extended channels 73 also may help improve fluid transportation and distribution along the length of the deposits of superabsorbent polymer particles within the absorbent layer 71, and thereby may help speed liquid absorption.

Alternatively, the longitudinal channels may be curved and/or arcuate. Longitudinally extended but curved channels may also serve as hinge structures in the absorbent core structure which may help enable the absorbent core structure to flex laterally and thereby conform to the wearer's anatomy along the transverse direction in the crotch region. Thus, the channels may contribute to imparting a comfortable and superior fit in addition to permitting improved liquid transportation and distribution.

Longitudinally-oriented channels formed in the absorbent layer may help transport and distribute liquid (e.g., urine) along the lengths of the deposits of superabsorbent polymer particles in the absorbent layer, and thereby help speed acquisition and absorption. However, the correspondingly-defined longitudinal chambers or other structures containing or defining the deposits of superabsorbent polymer particles may develop elevated internal pressure as the particles absorb liquid, swell, and press against each other. This pressure may have a longitudinal, structural stiffening effect on the absorbent core structure. The internal pressure causes the absorbent layer to tend to straighten longitudinally, rather than easily curve around and beneath the wearer's lower torso as the absorbent core structure wraps between the wearer's legs. This stiffening effect may help prevent creation of a droopy or saggy appearance of the article when wetted. On the other hand, it has been discovered that this stiffening effect can cause the frontward and rearward ends of the absorbent core structure to bulge away from the wearer's body in frontward and rearward directions, creating noticeable, unsightly, and potentially uncomfortable bulges proximate the front and rear edges of the absorbent layer. It has been discovered that this effect may be mitigated by one or more of several alternative configurations in a pant structure.

As suggested in FIG. 5, the absorbent layer 71 may include additional lateral channels 74 to further increase the fluid transportation and/or improve fit of the pant. The above description of channels may equally apply to any of lateral channels 74. The lateral channels may be straight, as suggested in FIG. 5, or may be curved, but their longer dimension is preferably more aligned with the lateral direction than the longitudinal direction.

As suggested in FIG. 5, in some examples the absorbent layer also may include one or more lateral channels 74. Lateral channels 74 may have their longer dimensions oriented predominately in the lateral direction, or even be substantially perpendicular to the longitudinal axis 200 of the pant (shown in FIG. 2). Lateral channels 74 may serve as transverse hinge structures that can enable the absorbent core structure to flex longitudinally thereabout, and thereby conform to the wearer's anatomy along the longitudinal direction as it wraps around and beneath the wearer's lower torso between the legs from front to back. This may help mitigate the longitudinal stiffening that may occur as absorbent layer 71 becomes loaded with urine, which may be exacerbated by longitudinal channels.

Lateral channels 74 may extend over a distance of at least 10%, or at least 15%, or at least 20%, of the lateral dimension of the absorbent layer 71. They may extend up to 90% of the lateral dimension of the absorbent layer 71. The lateral channels 74 may extend up to 30% or 45% of the lateral dimension of the absorbent layer 71. In some examples, lateral channels 74 may connect longitudinal channels 73, as suggested in FIG. 5. In some examples, lateral channels 74 may be distinct and separate from longitudinal channels 73.

In some examples, the structure of absorbent layer 71 defining the channels 73 and/or 74 and corresponding unchanneled volumes containing deposits of superabsorbent polymer particles may be imparted with features that cause the structure to change from a first configuration when dry to a second configuration when wetted to, e.g., one-quarter, one-third, one-half, two-thirds or more of the total absorbent capacity (by weight of absorbed liquid) of the absorbent layer. For example, materials used to form chambers or other structures containing or defining discrete deposits of superabsorbent polymer particles, and defining channels among/between them, may be configured to change structure when wetted. In one example, an absorbent core structure 65 may have a first configuration when dry and a second configuration when wetted, e.g., to more than half of its absorbent capacity. One mechanism that may be used to enable this may be a water soluble or otherwise releasable adhesive affixing the substrate layers enveloping the superabsorbent polymer particles, and defining, the channels. Upon wetting and/or outward pressure against the substrate layers from swelling deposits of superabsorbent polymer particles, the adhesive releases, and the swelling deposits of superabsorbent polymer particles are permitted to expand into the volume previously defined by the channels, which then may reduce in size or even disappear. This may have the effect of relieving pressure within the absorbent layer 71 and absorbent core structure 65, which may lessen the longitudinal stiffening effects described above. Thus, advantages of channels (flexibility, conformability and liquid distribution enhancement) may be enjoyed at times before the pant is substantially wetted, while a disadvantage of channels (stiffness) may be mitigated at times after the pant has been substantially wetted.

This changing channel structure may be utilized alone or may be combined with permanent channel structures of any desired configuration, including but not limited to any configuration described herein.

The absorbent layer, absorbent core structure and/or configuration of channels may also have any features described in U.S. Pat. App. Pub. Nos. US2014/0163511; US2014/0163503; US2014/0163501; US2014/0163500; US2012/0316526; US2012/0316528; US2014/0163501; and US2014/0371701; and U.S. patent application Ser. No. 14/598,783.

In some examples, as suggested in FIGS. 3, 4A-4C and 5-7, the absorbent core structure 65 may include an acquisition layer 72, disposed between the topsheet and the wearer-facing side of the absorbent layer 71. The acquisition layer 72 may be formed of one or more materials providing an open, highly porous structure configured to disperse and dissipate mechanical energy in a flow of urine, while providing interstitial spaces within the structure to serve as a temporary reservoir for the urine until the absorbent layer 71 can capture and retain (absorb) it. The acquisition layer 72 may consist of a single layer or multiple sublayers, such as an upper acquisition sublayer closest wearer's skin and a lower acquisition sublayer disposed between the upper acquisition layer and the absorbent layer 71. The acquisition layer 72 may be disposed so as to be in direct contact with the absorbent layer. Where channels are present in the absorbent layer 71, materials forming the acquisition layer 72 may extend into or fill in the channels or portions thereof; this may be preferred in some circumstances to prevent rapid, unrestricted flow of unabsorbed urine through the channels, which could increase chances of leakage. In some examples, the acquisition layer, or a sublayer thereof, may be bonded to the substrate layer which defines the channels, thus providing a matching surface profile to the acquisition layer.

Acquisition layer 72 may have the form of, e.g., a layer, mat or other body formed of or including, e.g., comminuted cellulose fibers, or other hydrophilic natural, semi-synthetic or synthetic fibers or other material that may be used to form a mat, layer or other body.

In one example, one or both of upper and lower acquisition sublayers may include a non-woven mat of fibers, which may be hydrophilic. Further, according to a certain example, one or both of the upper and lower acquisition layers may include the chemically cross-linked cellulosic fibers, which may or may not form part of a nonwoven material. According to an example, the upper acquisition layer may include a nonwoven, without the cross-linked cellulosic fibers, and the lower acquisition layer may include the chemically cross-linked cellulosic fibers. Further, according to an example, the lower acquisition layer may include the chemically cross-linked cellulosic fibers mixed with other fibers such as natural or synthetic polymeric fibers. According to example examples, such other natural or synthetic polymeric fibers may include high surface area fibers, thermoplastic binding fibers, polyethylene fibers, polypropylene fibers, PET fibers, rayon fibers, lyocell fibers, *eucalyptus* fibers and mixtures thereof. Suitable non-woven materials for the upper and lower acquisition layers include, but are not limited to SMS material, including a spunbonded, a meltblown and a further spunbonded layer. In certain examples, permanently hydrophilic nonwovens, and in particular, nonwovens with durably hydrophilic coatings are desirable. Another suitable example includes an SMMS-structure. In certain examples, the nonwovens are porous.

Close Fit and Discreetness-Enhancing Features

Core Channels

As described above, the absorbent layer 71 may be formed with one or more channels 73, 74. For purposes herein, it may be desired that the absorbent layer have at least one lateral channel 74, disposed no more than 20 percent of the overall length L of the absorbent core structure from the front edge 61 of the absorbent core structure. (For purposes herein, length L of the absorbent core structure 65 is measured from the forwardmost front edge 61 to the rearwardmost rear edge 62, of the combined absorbent layer 71 and acquisition layer 72 (if present).) Such a lateral channel may serve as a hinge, providing a lateral line of flexure that enables the forward portion of the absorbent core structure to more easily flex toward the wearer in response to the forces exerted by the belt (front and rear panel) structure, and thereby better conform to the wearer's anatomical features, enhancing close fit, reducing chances of leakage, and improving discreetness of appearance of the pant. For similar reasons, it may be desired that the absorbent layer have a second lateral channel 74, disposed no more than 20 percent of the overall length L from the rear edge 62 of the absorbent core structure.

Acquisition layer 72 may also have one or more channels therein (not specifically shown), for purposes of further enhancing flexibility of the absorbent core structure 65. Acquisition layer 72 may have one or more channels that are aligned with/superadjacent to channels present in absorbent layer 71 in plan, such that thin areas of the absorbent core structure defined by aligned, superadjacent/subjacent channels, present in both absorbent layer 71 and acquisition layer 72, work together to provide flexible "hinge" areas through the entire absorbent core structure 65. Alternatively, channels in the absorbent layer 71 and channels in the acquisition layer 72 may be offset in plan, such that overall flexibility of the absorbent core structure 65 is enhanced by the channels, but there are not sharply defined hinge regions created by aligned superadjacent/subjacent channels in the absorbent layer 71 and acquisition layer 72.

In other examples, the acquisition layer 72 may be formed with one or more channels in arrangements described above for the absorbent layer 71 and depicted in the figures, while the absorbent layer 71 is not channeled. This configuration may be desired in structures in which the absorbent layer 71 is relatively thin (in the z-direction), and/or already inherently more flexible, than the acquisition layer 72.

Tapered Absorbent Core Structure; Profiled Distribution of Absorbent Materials

As may be appreciated from FIGS. 3 and 4C, one or more layers of the absorbent core structure 65 may be tapered such that their z-direction thickness diminishes toward the end and side edges. This feature, alone or in combination with inclusion of channels, also enables such portions to more easily flex toward the wearer in response to the forces exerted by the belt (front and rear panel) structure, and thereby better conform to the wearer's anatomical features, enhancing close fit, reducing chances of leakage, and improving discreetness of appearance of the pant. Additionally, relatively thin lateral and/or longitudinal edges of the absorbent core structure 65 resulting from tapering reduces the possibility that the edges will create well-defined and visible discontinuities or bulges in the outer profile of the pant while it is worn, and thus, improve discreetness of the pant beneath outer clothing. It may be desired that one or more layers of the absorbent core structure 65 be tapered toward reducing thickness approaching the edges at least in the rearward portion(s) thereof, but also in both the rearward and frontward portions as reflected in FIG. 2, and in some examples, in both the rearward and frontward portions, and also toward each longitudinal edge 63, 64 as may be appreciated from FIG. 4C. In addition to making the edges of the absorbent core structure less obtrusive, tapering enables a profiled distribution of absorbent materials so that they are concentrated in regions more proximate the forward region of the wearer's crotch area, slightly forward of the longitudinal midpoint of the pant, where many types of outer clothing may not fit or lay as closely/tightly to the wearer as they do about, e.g., the waist and buttocks areas, and where urine is discharged, further enhancing its capture and absorption.

Tapering may be reflected in basis weight(s) of the one or more layer(s) of the absorbent core structure that vary in localized regions of the absorbent core structure. In one example, referring to FIG. 3, the length L of the absorbent core structure 65 may be divided into five equal sublengths SL1, SL2, SL3, SL4 and SL5, from front to rear. Tapering down in thickness toward the front and rear edges 61, 62, and profiled distribution of absorbent core materials, may be reflected in one or more of the following relationships: Reflecting a concentration of absorbent materials forward of the longitudinal midpoint of the pant, the total of the average basis weights of all materials in the first and second sublengths SL1 and SL2 may be greater than the total of the average basis weights of all materials in the fourth and fifth sublengths SL4 and SL5. Further reflecting a concentration of absorbent materials forward of the longitudinal midpoint of the pant, the average basis weight of all materials in the second sublength SL2 may be greater than the average basis weight of all materials in any of the other sublengths SL1, SL3, SL4, SL5. Reflecting tapering at the front, the average basis weight of all materials in sublength SL1 may be less than the average basis weight of all materials in sublength SL2. Reflecting tapering at the rear, the average basis weight of all materials in sublength SL5 may be less than the average basis weight of all materials in sublength SL4.

If tapering at the longitudinal edges of the absorbent core structure is included, referring to FIG. 4C, in one example, the width W of the absorbent core structure 65 may be divided into three equal subwidths SW1, SW2 and SW3, from side to side (leftmost edge 63 to rightmost edge 64). Tapering down in thickness toward the leftmost and rightmost edges 63, 64, and profiled distribution of absorbent core materials, may be reflected in one or more of the following relationships: Reflecting a concentration of absorbent materials in the central portion of the absorbent core structure, the average basis weight of all materials in the second subwidth SW2 may be greater than each of the average basis weights of all materials in the first and third subwidths SW1 and SW3. This relationship also may reflect tapering down of thickness toward the longitudinal edges of the absorbent core structure 65.

Figure 6:
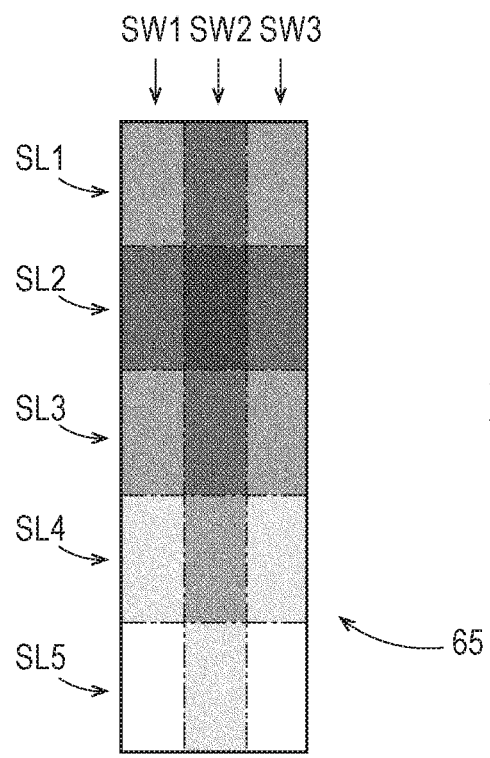
FIG. 6 is a schematic plan view of an absorbent core structure, graphically depicting possible variations in average basis weights of regions of the structure.

These relationships present in combination are graphically, schematically illustrated in FIG. 6. The area of greatest material basis weight is shown with the darkest shading (area SL2-SW2). Shading becomes lighter with decreasing basis weight, and the areas of least basis weight are shown with no shading (areas SL5-SW1 and SL5-SW3).

For purposes herein, the "average basis weight of all materials" in a sublength or subwidth of an absorbent core structure may be determined by identifying the absorbent core structure layers as described herein, in samples of the article in question, measuring the absorbent core structure total length and width, physically dividing them into five equal sublengths or 3 equal subwidths according to the measurement desired, weighing each of the sublength and/or subwidth portions and dividing each such weight by the associated surface area to calculate an average basis weight for each such localized region. Absorbent core structures that are rectangular in shape (in plan view) are generally more easily and efficiently manufactured than those that are not. For absorbent core structures that are not rectangular in shape as depicted herein, however, the length L and width W thereof are, respectively, the length at the longest portion and the width at the widest portion.

Tapering and localized variations in basis weights of materials in the absorbent core structure 65 as described above may be included in either or both of absorbent layer 71 and acquisition layer 72, and may also be included in the distribution of particles of SAP across the length L and width W of the absorbent core structure, in the distribution of cellulose or polymer fibers included in the absorbent core structure across the length L and width W of the absorbent core structure, or a combination thereof.

Figure 7:
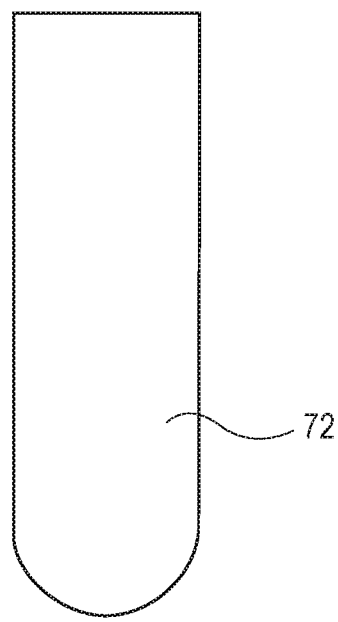
FIG. 7 is a schematic plan view of an acquisition layer component of an absorbent core structure.

Additionally, the overall absorbent core structure 65 may be tapered or graduated down in thickness toward the edges thereof by using an acquisition layer 72 having smaller length and/or width dimensions than those of the absorbent layer 71. Referring to FIGS. 5 and 7, for example, the length of acquisition layer 72 may be less than the length of absorbent layer 71. Its location of placement over absorbent layer 71 with the front edges of each aligned, causes the rear edge of the acquisition layer to lie short of the rear edge of the absorbent layer, and as a result, the overall thickness of the absorbent core structure 65 to be reduced in the rear portion proximate the rear edge. Alternatively, both the front and rear edges of the acquisition layer may lie short of the respective front and rear edges of the absorbent layer. One or both of the absorbent layer 71 and acquisition layer may also have rounded corners in the front or rear. As depicted in FIG. 5, the acquisition layer has a rounded rear edge profile. This may help reduce or remove sharp corners from potential prominence in the outward profile of the pant during wear.

Elastic Members Placement, Spacing and Prestrain Variance

As explained above, use of longitudinally-spaced, laterally-extending elastomeric strands, rather than elastic film, may be preferred to elasticize the belt structure. Among other benefits, spaced strands provide superior breathability to the belt structure. Further toward the purpose of producing a close-fitting, discreet pant, additional aspects of placement and spacing of elastic members may be desired.

A number of disposable absorbent pants currently marketed for use by adults suffering from incontinence include elastomeric strands to elasticize the belt structure. However, they often do not have strands that laterally traverse the absorbent pad assembly, absorbent core structure, or components thereof, from one longitudinal edge to the other. In some products, lateral elastic strands are not included in portions of the belt structure lying longitudinally below forward and/or rearward ends/edges of the absorbent pad assembly and/or components thereof. In some products, lateral elastic strands are present in portions of the belt structure lying longitudinally below forward and/or rearward ends/edges of components of the absorbent pad assembly, but do not traverse the assembly, or are cut proximate the longitudinal edges of the assembly, or are deactivated (have elasticity removed or rendered inoperable) along portions of their lengths that traverse the absorbent pad assembly. While such configurations may have other useful purposes and functions, they tend to allow the forward and/or rearward portions of the absorbent pad assembly to bulge outwardly (away from the wearer). Many wearers find such bulges undesirable or even unacceptable as they tend to create corresponding bulges in outer clothing and make it visually apparent that an incontinence pant is being worn.

Referring to FIGS. 2 and 3, to substantially reduce the number and prominence of such bulges, it may be desired that laterally extending, prestrained elastic strands 40 included in the belt structure laterally traverse the absorbent pad assembly 50 over portions thereof present in the front and rear waist regions of the pant and are active over such portions. In the front panel 20, it may be desired that elastic stands 40 traverse a front portion of the length PL of the absorbent pad assembly, i.e. front covered length FCL, that is at least 15 percent, more preferably at least 20 percent, of length PL. In the rear panel 30, it may be desired that elastic strands 40 traverse a rear portion of the length PL of the absorbent pad assembly, i.e. rear covered length RCL, which is at least 30 percent, more preferably at least 35 percent, and even more preferably at least 40 percent, of length PL. For purposes herein, and as reflected in FIG. 2, the covered length FCL or RCL is measured, respectively, from the front 51 or rear 52 end of the absorbent pad assembly 50, to the lowermost extent of the lowermost elastic strand 40 laterally traversing the absorbent pad assembly 50, with the pant separated at the side seams 13 as suggested in FIG. 2. When prestrained elastic strands are so disposed, they tend to urge the forward and rearward portions of the absorbent pad assembly, particularly along the longitudinal edges thereof, toward the wearer, thereby minimizing outward bulging of the absorbent pad assembly.

It may be desired that the strands be longitudinally spaced relatively more closely than is typical, at least in the portions of the belt structure and front rear panels 20, 30 thereof that are disposed above the lower ends of the side seams 13. Thus, at least in these portions of the front and/or rear panels 20, 30, it may be desired that the average longitudinal spacing SS of one or more groups of adjacent lateral elastic strands be no greater than 10 mm, more preferably no greater than 7 mm and still more preferably no greater than 5 mm. (As previously noted, longitudinal spacing between adjacent elastic strands is to be understood to refer to the distance between their longitudinal axes, not the distance between their nearest outer surfaces.) In addition to imparting a more cloth-like appearance to the belt structure as previously noted, this relatively close longitudinal spacing of elastic strands in these portions of the belt structure helps provide somewhat concentrated but still well-distributed pressure against such forward and rearward ends/edges of the absorbent pad assembly, urging them toward the wearer's body and thereby tending to minimize bumps and bulges in these areas of the belt structure.

Additionally, a number of disposable absorbent pants currently marketed for use by adults suffering from incontinence, while including laterally-extending elastomeric strands to elasticize the belt structure, have no lateral elastomeric strands disposed in the rear panel, in areas below the side seams 13. Some products have substantial areas of unelasticized nonwoven material forming an outer layer, which is uncontrolled about the outer areas of the buttocks proximate the leg openings, which can impart a loose look and feel about the leg openings in these areas which some wearers may find undesirable. Other products may include elastic members disposed along the materials about the leg openings to cause the materials to gather as leg bands, but still leave substantial areas above the leg opening edges uncontrolled, creating a bloused look which some wearers may find undesirable. Additionally, inclusion of profiled leg band elastic members introduces added complexity and expense to the manufacturing process.

It has been discovered that inclusion of a number of laterally-extending elastic strands 40 below the side seams 13 in the rear panel 30 (i.e., below rear seam areas 13b) as suggested in FIG. 2, has substantial beneficial effect controlling the material about the leg openings and about the outer areas of the buttocks, thereby providing the appearance of a closer, more tailored fit. Additionally, inclusion of such additional laterally-extending elastic strands 40 in panel materials below the side seams 13 is generally more simple and inexpensive in the manufacturing process, than inclusion of profiled leg band elastic members.

Accordingly, it may be desired that a plurality of laterally-extending elastic strands 40 be included at least in rear panel 30, in areas below the bottoms of side seams 13. Referring to FIG. 2, for suitable control of rear leg edges below side seams 13, an elasticized portion of the rear panel below the bottoms of the side seams and having a length REP of at least 5 percent, more preferably at least 10 percent, even more preferably at least 15 percent, and still more preferably at least 20 percent, of the overall length OL of the pant structure, may include laterally-extending elastic strands 40.

For similar reasons, one or more laterally-extending elastic strands 40 may be included in front panel 20, in areas below the bottoms of side seams 13

It may be desired, however, that any such laterally-extending elastic strands below the side seams have either, or a combination of, longitudinal spacing and prestrain amount that differs from those of the lateral elastic strands above the side seams. In particular, as suggested by FIG. 2, it may be desired that the average longitudinal spacing of elastic strands 40 disposed below the side seams 13 be greater than the average longitudinal spacing of elastic strands 40 disposed above the side seams 13. Accordingly, all or a subset of elastic strands disposed in rear panel 30 below the side seams 13 may have an average longitudinal spacing SS of 5 mm or more, 7 mm or more, or even 10 mm or more. Alternatively, or in combination with such spacing, it may be desired that the average amount of prestrain imparted to the elastic strands 40 disposed below the side seams 13 be less than the average amount of prestrain imparted to the elastic strands 40 disposed above the side seams 13. These variations may help ensure that the material of the rear panel 30 below the side seams 13 is not excessively pulled laterally inward toward longitudinal axis 200, reducing coverage of the outer regions of the wearer's buttocks to an undesirable extent. Additional configurations of elastic strands in panels 20, 30 suitable for these purposes are disclosed in U.S. Prov. App. Ser. No. 62/332,496.

Location of Longitudinal Elastic Members

Figure 8:
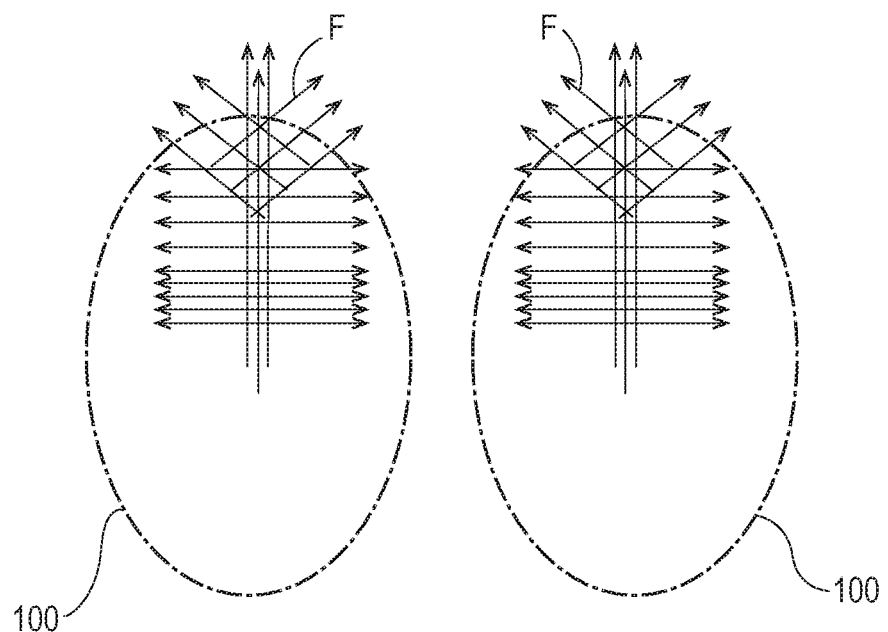
FIG. 8 is a schematic illustration of tensile forces that may be present in zones of a pant structure when elastic members in the pant structure are stretched.

Referring to FIGS. 2, 4A and 8, it has been discovered, additionally, that particular disposition of longitudinally-oriented, left and right pad assembly edge elastic members 69, 70 relative lateral elastic members 40 in the rear panel 30, can have beneficial effects.

When appropriately located, and in some circumstances when active portions of prestrained longitudinal elastic members 69, 70 proximate the longitudinal left and right edges 67, 68 of the absorbent pad assembly 50 cross active portions of prestrained lateral elastic strands 40 in crossing zones 100 located in rear panel 30, the tensile forces in the respective prestrained elastic members combine to produce forces F (FIG. 8) in the rear panel 30 that tend to draw the panel material, and the underlying materials of the absorbent pad assembly 50, into the wearer's intergluteal cleft. This effect further contributes to imparting a close and discreet fit to the pant in the rear portion. To enable this effect, however, the longitudinal elastic members 69, 70 should be located closer to the longitudinal axis 200 of the pant, than to the rear seam area 13b; i.e., distance ESC is less than distance ESS as reflected in FIG. 2, i.e., toward the center of the pant in the lateral direction. (ESC and ESS are measured in the lateral direction.)

Absorbent Capacity Features

Various combinations of the features described above can provide for a pant structure that has an improved, discreet fit and profile while worn, while still having an absorption capacity required by users with "moderate" and "heavy" incontinence needs. Thus, the absorbent core structure of the pant may still include at least 3 grams of superabsorbent polymer materials for a "moderate" needs product, or at least 5 grams of superabsorbent polymer materials for a "heavy" needs product, included in an absorbent layer. The absorbent core structure of the pant may still include at least 1 gram of cellulose and/or polymer fiber, included in an absorbent layer, an acquisition layer or a combination thereof.

The following examples are contemplated within the scope of the description herein:

1. A low-bulk, high capacity disposable absorbent pant, comprising:

front and rear panels (20, 30) each comprising stretch laminate material, the stretch laminate material comprising an inner layer (21, 31) and an outer layer (22, 32), each of the inner and outer layers being formed of nonwoven web material, and a plurality of longitudinally spaced, laterally extending and laterally prestrained elastomeric panel strands (40) disposed between the inner layer and the outer layer, wherein the front and rear panels are joined to each other along left and right side seams (13) each having a top end and a bottom end; and an absorbent pad assembly (50) comprising:

a front portion terminating at a front end (51) and a rear portion terminating at a rear end (52), the front portion being joined to the front panel at a front joined location such that the front end is disposed above the bottom ends of the side seams, and the rear portion being joined to the rear panel at a rear joined location a such that the rear end is disposed above the bottom ends of the side seams, a liquid permeable topsheet (60), a liquid impermeable backsheet (66), and an absorbent core structure (65) disposed between the topsheet and the backsheet;

a left edge (67) and a right edge (68), at least one longitudinally extending, prestrained left pad assembly elastomeric member (69) disposed along the left edge (67) within 10 mm thereof, and at least one longitudinally extending, prestrained right pad assembly elastomeric member (70) disposed along the right edge (68) within 10 mm thereof, wherein the left pad assembly elastomeric member and the right pad assembly elastomeric member are each disposed at a location that is closer to a longitudinal axis (200) of the pant than to the respective left or right side seam (13) of the pant, left and right longitudinal barrier cuffs (80, 81) having respective left and right barrier cuff proximal portions (82, 83) joined to another component of the absorbent pad assembly, and left and right barrier cuff free edges (84, 85), each barrier cuff being configured such that the barrier cuff free edge may extend away from the topsheet, each of the barrier cuffs further comprising at least one longitudinally extending, longitudinally prestrained barrier cuff elastomeric member (86, 87) disposed within 10 mm of the respective free edge thereof;

wherein a sub-plurality of the prestrained elastomeric panel strands (40) in the front panel (20) overlie and traverse the front portion of the absorbent pad assembly to the outside thereof, and a sub-plurality of the prestrained elastomeric panel strands (40) in the rear panel (30) overlie and traverse the rear portion of the absorbent pad assembly to the outside thereof.

2. The pant of example 1 wherein an active portion each of the left and right pad assembly elastomeric members (69, 70) crosses one or more of the sub-plurality of prestrained elastomeric panel strands (40), within a crossing zone (100) in the rear panel (30).

3. The pant of either of the preceding examples wherein the absorbent core structure (65) is tapered or graduated down in thickness toward one or both of a front edge (61) and a rear edge (62) thereof.
4. The pant of any of the preceding examples wherein the absorbent core structure (65) is tapered or graduated down in thickness toward longitudinal side edges (63, 64) thereof
5. The pant of any of the preceding examples wherein the absorbent core structure (65) comprises an absorbent layer (71) comprising particles of superabsorbent polymer.
6. The pant of example 5 wherein the absorbent core structure (65) comprises an acquisition layer (72) comprising cellulose and/or polymer fibers.
7. The pant of any of the preceding examples wherein the absorbent core structure (65) comprises:
   a front edge (61) and a rear edge (62), the front edge and the rear edge defining an absorbent core length L,
   wherein the absorbent core length L has first, second, third, fourth and fifth equal sublengths (SL1-SL5) thereof, measured from the front edge (61) to the rear edge (62), respectively;
   wherein each of the first, second, third, fourth and fifth equal sublengths of the absorbent core has an average basis weight of absorbent core structure materials; and
   wherein the total of the average basis weights of absorbent core structure materials in the fourth and fifth sublengths is less than the total of the average basis weights of absorbent core structure materials in the first and second sublengths.
8. The pant of any of the preceding examples wherein all or a majority of the plurality of elastomeric panel strands (40) in the rear panel (30) and/or the front panel (20), disposed above the bottoms of the side seams (13), have an average longitudinal spacing SS of less than 10 mm, more preferably less than 7 mm, and even more preferably less than 5 mm.
9. The pant of any of the preceding examples wherein all or a majority of the plurality of elastomeric panel strands (40) in the rear panel (30) and/or the front panel (20), disposed above the bottoms of the side seams (13), have an average size of from 400 to 1000, more preferably from 500 to 900, and even more preferably from 600 to 800 decitex.
10. The pant of any of the preceding examples wherein all or a portion of the plurality of elastomeric panel strands (40) in the rear panel (30) and/or the front panel (20) disposed above the bottoms of the side seams (13), have an average level of prestrain of from 50% to 290%, more preferably from 90% to 230%, and still more preferably from 120% to 180%.
11. The pant of any of the preceding examples wherein the absorbent core structure has a rectangular shape.
12. The pant of any of the preceding examples wherein the rear panel (30) comprises a first group of the laterally extending elastomeric panel strands (40) disposed above the bottom ends of the side seams (13), and second group of the laterally extending elastomeric panel strands (40) disposed below the bottom ends of the side seams (13).
13. The pant of example 12 wherein the first group of elastomeric panel strands has a first average longitudinal spacing (SS) that is less than a second average longitudinal spacing (SS) of the second group of elastomeric panel strands.
14. The pant of example 12 wherein the first group of elastomeric panel strands has a first average level of prestrain that is greater than a second average level of prestrain of the second group of elastomeric panel strands.
15. The pant of example 5 or any other example dependent thereon comprising one or more channels (73) extending longitudinally through the absorbent layer (71).
16. The pant of example 5 or any other example dependent thereon comprising one or more channels (74) extending laterally through the absorbent layer (71).
17. The pant of any of the preceding examples wherein the absorbent core structure (65) comprises at least 3 grams of particles of superabsorbent polymer.
18. The pant of any of the preceding examples wherein the absorbent core structure (65) comprises at least 1 grams of cellulose and/or polymer fibers.

The dimensions and values disclosed herein are not to be understood as being strictly limited to the exact numerical values recited. Instead, unless otherwise specified, each such dimension is intended to mean both the recited value and a functionally equivalent range surrounding that value.

Every document cited herein, including any cross referenced or related patent or application, is hereby incorporated herein by reference in its entirety to the extent not inconsistent herewith, unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:
1. A low-bulk, high capacity disposable absorbent pant, comprising:
   front and rear panels each comprising stretch laminate material, the stretch laminate material comprising an inner layer and an outer layer, each of the inner and outer layers being formed of nonwoven web material, and a plurality of longitudinally spaced, straight, laterally extending and laterally prestrained elastomeric panel strands disposed between the inner layer and the outer layer,
      wherein the front and rear panels are joined to each other along left and right side seams each having a top end and a bottom end; and
   an absorbent pad assembly comprising:
      a front portion terminating at a front end and a rear portion terminating at a rear end, the front portion being joined to the front panel at a front joined location such that the front end is disposed above the bottom ends of the side seams, and the rear portion being joined to the rear panel at a rear joined location a such that the rear end is disposed above the bottom ends of the side seams,
      a liquid permeable topsheet, a liquid impermeable backsheet, and an absorbent core structure disposed between the topsheet and the backsheet;
      a left edge and a right edge, at least one longitudinally extending, prestrained left edge elastic member disposed along the left edge within 10 mm thereof, and at least one longitudinally extending, prestrained right edge elastic member disposed along the right edge within 10 mm thereof, wherein the left edge assembly elastomeric member and the right edge assembly elastomeric member are each disposed at a location that is closer to a longitudinal axis of the pant than to the respective left or right side seam of the pant, left and right longitudinal barrier cuffs having respective left and right barrier cuff proximal portions joined to another component of the absorbent pad assembly, and left and right barrier cuff free edges, each barrier cuff being configured such that the barrier cuff free edge may extend away from the topsheet, each of the barrier cuffs further comprising at least one longitudinally extending, longitudinally prestrained barrier cuff elastomeric member disposed within 10 mm of the respective free edge thereof;

wherein a sub-plurality of the prestrained elastomeric panel strands in the front panel overlie and completely traverse the front portion of the absorbent pad assembly to the outside thereof, and a sub-plurality of the prestrained elastomeric panel strands in the rear panel overlie and completely traverse the rear portion of the absorbent pad assembly to the outside thereof;

wherein the plurality of the prestrained elastomeric panel strands in the rear panel comprises a first group disposed above the bottoms of the side seams and a second group disposed below the side seams, and strands in both the first and second groups overlie and completely traverse the rear portion of the absorbent pad assembly to the outside thereof; and wherein the plurality of prestrained elastomeric panel strands in the rear panel has an average longitudinal spacing SS no greater than 10 mm.

2. The pant of claim 1 wherein an active portion each of the left and right pad assembly elastomeric members crosses one or more of the sub-plurality of prestrained elastomeric panel strands, within a crossing zone in the rear panel.

3. The pant of claim 1 wherein the absorbent core structure is tapered or graduated down in thickness toward one or both of a front edge and a rear edge thereof.

4. The pant of claim 1 wherein the absorbent core structure is tapered or graduated down in thickness toward longitudinal side edges thereof.

5. The pant of claim 1 wherein the absorbent core structure comprises an absorbent layer comprising particles of superabsorbent polymer.

6. The pant of claim 5 wherein the absorbent core structure comprises an acquisition layer comprising cellulose and/or polymer fibers.

7. The pant of claim 5 comprising one or more channels extending longitudinally through the absorbent layer.

8. The pant of claim 5 comprising one or more channels extending laterally through the absorbent layer.

9. The pant of claim 1 wherein the absorbent core structure comprises:
   a front edge and a rear edge, the front edge and the rear edge defining an absorbent core length L,
   wherein the absorbent core length L has first, second, third, fourth and fifth equal sublengths (SL1-SL5) thereof, measured from the front edge to the rear edge, respectively;
   wherein each of the first, second, third, fourth and fifth equal sublengths of the absorbent core has an average basis weight of absorbent core structure materials; and
   wherein the total of the average basis weights of absorbent core structure materials in the fourth and fifth sublengths is less than the total of the average basis weights of absorbent core structure materials in the first and second sublengths.

10. The pant of claim 1 wherein the plurality of elastomeric panel strands in the front panel have an average longitudinal spacing no greater than 10 mm.

11. The pant of claim 1 wherein all or a majority of the plurality of elastomeric panel strands in the rear panel and/or the front panel, disposed above the bottoms of the side seams, have an average size of from 400 to 1000 decitex.

12. The pant of claim 1 wherein all or a portion of the plurality of elastomeric panel strands in the rear panel and/or the front panel disposed above the bottoms of the side seams, have an average level of prestrain of from 50% to 290%.

13. The pant of claim 1 wherein the absorbent core structure has a rectangular shape.

14. The pant of claim 1 wherein the first group has a first average longitudinal spacing that is less than a second average longitudinal spacing of the second group.

15. The pant of claim 1 wherein the first group has a first average level of prestrain that is greater than a second average level of prestrain of the second group.

16. The pant of claim 1 wherein the absorbent core structure comprises at least 3 grams of particles of superabsorbent polymer.

17. The pant of claim 1 wherein the absorbent core structure comprises at least 1 gram of cellulose and/or polymer fibers.

* * * * *